(12) United States Patent
Airaksinen et al.

(10) Patent No.: US 7,959,811 B2
(45) Date of Patent: Jun. 14, 2011

(54) SEPARATION PROCESS

(75) Inventors: Jyrki Airaksinen, Espoo (FI); Heikki Heikkilä, Espoo (FI); Jari Lewandowski, Siuntio (FI); Kari Laiho, Kirkkonummi (FI); Päivi Sarmala, Rajamäki (FI)

(73) Assignee: Danisco A/S, Copenhagen K (DK)

( * ) Notice: Subject to any disclaimer, the term of this patent is extended or adjusted under 35 U.S.C. 154(b) by 0 days.

(21) Appl. No.: 12/711,563

(22) Filed: Feb. 24, 2010

(65) Prior Publication Data

US 2010/0213130 A1 Aug. 26, 2010

Related U.S. Application Data

(60) Provisional application No. 61/155,261, filed on Feb. 25, 2009.

(51) Int. Cl.
*B01D 15/08* (2006.01)
(52) U.S. Cl. ..... 210/659; 210/635; 210/656; 210/198.2; 127/46.2; 127/46.3
(58) Field of Classification Search .................. 210/635, 210/656, 659, 198.2; 127/46.2, 46.3, 55
See application file for complete search history.

(56) References Cited

U.S. PATENT DOCUMENTS

| | | | |
|---|---|---|---|
| 4,109,075 A | 8/1978 | Deaton | |
| 4,182,633 A | 1/1980 | Ishikawa et al. | |
| 4,267,054 A | 5/1981 | Yoritomi et al. | |
| 4,402,832 A | 9/1983 | Gerhold | |
| 4,487,198 A | 12/1984 | Miyake et al. | |
| 4,843,156 A | 6/1989 | Miyake et al. | |
| 5,127,957 A | 7/1992 | Heikkila et al. | |
| 5,637,225 A | 6/1997 | Heikkila et al. | |
| 6,093,326 A | 7/2000 | Heikkila et al. | |
| 6,200,390 B1 | 3/2001 | Kearney et al. | |
| 6,572,775 B2 | 6/2003 | Heikkila et al. | |
| 6,602,420 B2 | 8/2003 | Kearney et al. | |
| 6,685,781 B2 | 2/2004 | Hyöky et al. | |
| 6,896,811 B2 | 5/2005 | Heikkila et al. | |
| 2003/0173299 A1* | 9/2003 | Heikkila et al. ............. | 210/656 |
| 2010/0212662 A1* | 8/2010 | Airaksinen et al. ............. | 127/42 |

OTHER PUBLICATIONS

International Search Report and Written Opinion dated May 27, 2010 issued in respect of corresponding International Application No. PCT/FI2010/050126.

\* cited by examiner

*Primary Examiner* — Ernest G Therkorn
(74) *Attorney, Agent, or Firm* — Scully, Scott, Murphy & Presser, P.C.

(57) ABSTRACT

The present invention relates to a chromatographic separation process for fractionating solutions containing sugars, sugar alcohols, sugar acids and/or betaine by utilizing fractions comprising parts of the separation profile as a substituent of the eluent in a novel and inventive manner. The starting solutions are typically multicomponent plant-based extracts and hydrolysates, stillages, and fermentation products and derivatives thereof. The process prow vides improved separation capacity and separation efficiency without affecting the yield or purity of product components, such as sugars, sugar alcohols, sugar acids, and betaine. The process can especially be applied to sequential SMB separation systems.

32 Claims, 1 Drawing Sheet

FIGURE 1.

SEPARATION PROCESS

CROSS-REFERENCE TO RELATED APPLICATIONS

This application claims the benefit of U.S. Provisional Application No. 61/155,261 filed on Feb. 25, 2009.

FIELD OF THE INVENTION

The present invention relates to the field of chromatographic separation and especially to chromatographic fractionation of solutions containing sugars, sugar alcohols, sugar acids, and betaine by simulated moving bed and/or batch methods. The solutions are typically multicomponent plant-based extracts and hydrolysates and derivatives thereof. The process of the invention aims at improving the separation efficiency of the separation system by introducing fractions comprising parts of the separation profile back into the separation system in a novel and inventive manner to decrease the volume of the fresh eluent while essentially maintaining or even improving the yield and/or purity of the products.

BACKGROUND OF THE INVENTION

Chromatographic separation systems for separating valuable components, such as sugars and betaine, from plant-based extracts and hydrolysates and derivatives thereof, for example sulfite spent liquors, molasses, vinasse and starch hydrolysates, have been developed in recent years to improve the separation capacity and the separation efficiency of the systems. However, chromatographic separation systems, especially batch and also SMB systems, have the drawback that the ratio of eluent to feed has conventionally been rather high owing to the very complex nature of the systems. Various arrangements for circulating fractions of the eluate back to the separation system are already in use in chromatographic batch and SMB systems.

U.S. Pat. No. 4,109,075 (CPC International Inc.) discloses a process for separating saccharides for example from a starch conversion product by a batch chromatography method, wherein at least three different saccharide fractions with differing molecular weight were collected. The first saccharide fraction (the highest molecular weight fraction) is then used for elution of the next feed, followed by elution with water. It is recited that this mode of operation minimizes the amount of eluent water and produces fractions rich in any one of lower saccharides $DP_1$ through $DP_4$.

U.S. Pat. No. 4,267,054 (Sanmatsu Kogyo Co.) discloses a batch chromatographic separation process for separating two components (such as glucose and fructose) from a multicomponent mixture, where the eluate coming from the separation column is collected in four fractions (a), b), (c) and (d). Fractions (a) and (c) are product fractions, fraction (b) is a mixed fraction containing relatively large amounts of the target products, and fraction (d) comprises a dilute fraction of the tail of fraction (c) and the head of fraction (a) used in the next cycle of operation. Fractions (b) and (d) are returned to the separation system by introducing them to the top of the separation column.

U.S. Pat. No. 4,402,832 (UOP Inc.) discloses a process for separating an extract component (such as fructose) from a raffinate component (such as glucose) in an SMB chromatographic system, where a dilute extract fraction and an impure raffinate fraction are returned to the same column from which they are collected. It is recited that the process provides considerable savings in the energy required to recover the eluent from the product streams as compared to prior art processes. Furthermore, it is recited that a reduced rate of fluid circulation through the separating units is achieved, which enables denser packing of the columns. This, in turn, is recited to minimize channelling through the adsorbent bed and to minimize void volume.

U.S. Pat. No. 4,487,198 (Hayashibara) disloses a dual stage chromatographic batch process for separating maltose from sugar starch solutions, where the eluate coming from the separation column in the first stage is collected in five fractions A, B, C, D and E. Fraction A is a dextrin fraction, fraction C is a maltose fraction and fraction E is a glucose fraction. Fraction B is a rear slope fraction containing dextrin with maltose impurities, and fraction D is a front slope fraction containing maltose with glucose impurities. In the next stage, fractions B and D are sequentially in this order applied to the separation column together with a fresh feed so that fraction B is introduced before the feed and fraction D after the feed.

U.S. Pat. No. 6,200,390 (Amalgamated Research Inc.) discloses a chromatographic continuous SMB process for recovering betaine and sugars from molasses, for example. In this process, a "block" of betaine is displaced from the circulation loop of the SMB system without disturbing the normal operation of the system. In practice, a betaine-concentrated fraction is withdrawn from the circulation loop of the continuous SMB system while an equal volume of water is introduced into the circulation loop. The circulation loop then continues without disruption.

U.S. Pat. No. 6,602,420 (Amalgamated Research Inc.) discloses a twostep chromatographic separation process with coupled looping; including a simulated moving bed operation coupled with continuous displacement chromatography (continuous SMB). The process may be applied to the recovery of betaine and/or invert sugar from sucrose solutions, such as molasses, to enable the subsequent production of a high purity sucrose product. It is recited that the use of displacement rather than elution provides reduction in the quantity of the eluent. It is stated that typical molasses chromatographic separation systems use ratios of about 6.0 to 8.0 water volume for each volume of feed molasses (60% dissolved solids in the feed), whereas the application of displacement chromatography permits organic compounds (such as betaine) to be separated with water-to-feed ratios of 2.0 or less. Furthermore, the concentration of the betaine fraction is recited to rise from a typical range of 1 to 5% dissolved solids to a range of 8 to 15% dissolved solids.

U.S. Pat. No. 5,127,957 (Danisco) discloses a chromatographic sequential SMB method having at least three columns for separating betaine, sucrose and rest molasses from molasses during the same cycle (one loop). In one embodiment of the process, a new portion of feed solution is added to the column series between partly separated rest molasses and sucrose fractions to the top of a preselected column.

U.S. Pat. No. 6,093,326 (Danisco) discloses a chromatographic two-loop SMB method comprising at least two packing material beds for processing a beet molasses based solution to recover a betaine fraction and a sucrose fraction.

In addition to beet molasses, the molasses solution may be for example cane molasses, stillage, vinasse wood molasses, wheat molasses, barley molasses or corn molasses.

U.S. Pat. No. 6,896,811 B2 (Danisco) discloses a chromatographic SMB method for fractionating a solution into at least two fractions by circulating the formed separation profile more than once or less than once through the chromatographic separation loop during one cycle (before the next feed is supplied to the separation system). The method may be applied for example to the separation of xylose from sulfite cooking liquor, sucrose and betaine from beet molasses, fructose from a fructose-containing syrup and maltose from a maltose-containing syrup.

U.S. Pat. No. 5,637,225 discloses a method of separating xylose from a sulfite cooking liquor by a chromatographic sequential SMB system comprising at least two chromatographic sectional packing material beds. The liquor to be separated is recycled in a recycling phase in one or more loops comprising one or more sectional packing material beds.

U.S. Pat. No. 6,572,775 discloses a method of fractionating a solution into two or more fractions by a chromatographic simulated moving bed process, wherein the separation comprises at least two separation profiles in the same loop. The method may be applied to the separation of betaine and sucrose from molasses, betaine from vinasse, glucose and fructose from a glucose/fructose mixture, and xylitol from a xylitol run-off, for example.

It appears from the above-described prior art that it is known to return fractions comprising different parts of the separation profile back to the separation columns. It also appears that the known arrangements provide reduced amounts of the eluent, savings in the energy required to recover the eluent from the product streams as well as higher purities of target component fractions. However, a need still exists for a more versatile separation process, where parts of the separation profile containing different fast moving and slow moving components are introduced back into different positions of the separation system as an eluent substitute to reduce further concentration costs and to enable the recovery of the components in desired target fractions while essentially maintaining or even improving the yield and purity of the product components.

DEFINITIONS RELATING TO THE INVENTION

"A product fraction" is a fraction taken out of the chromatographic separation process and comprising product components. There can be one or more product fractions.

"A residue fraction" or "a residual fraction" is a fraction which mainly contains components other than the product components, which are recovered. Said other components are typically selected from salts, organic acids and inorganic acids and salts thereof, for example acetic acid, xylonic acid, amino acids, color compounds, glycerol, lignosulfonates, oligosaccharides, etc., depending on the starting material as well as sugars, sugar alcohols and sugar acids other than the product sugars, sugar alcohols and sugar acids. There can be one or more residue fractions. The components of the residual fraction (other than the product components) are also referred to as "residual components". The nature of the residual components depends on the starting material. For example, in the separation of sugars, sugar alcohols and sugar acids from plant-based hydrolysates, such as sulfite spent liquor, the residual components of the residue fraction mainly comprise lignosulfonates, oligosaccharides, salts, organic acids (e.g. xylonic acid), and inorganic acids, etc. In the separation of fructose from mixtures of glucose and fructose, such as inverted sucrose and isomerized glucose, the residual components of the residual fraction mainly contain e.g. disaccharides and glucose. In the separation of betaine from sugarbeet based solutions, such as molasses or vinasse, the residual components of the residual fraction mainly comprise salts, color compounds, organic acids, amino acids, glycerol, mono-, di- and trisaccharides, etc. In the separation of maltose from starch hydrolysates, the residual components of the residual fraction are mainly composed of glucose, maltotriose, and higher malto-oligosaccharides.

"A recycle fraction" is a fraction, which contains incompletely separated product compounds, which has a lower purity or is more dilute than the product fractions and which is recycled back to the separation to be combined with the feed. The recycle fraction is typically used as diluent of the feed. There may also be one or more operations before returning the recycle to the column(s); for example, the recycle fraction(s) may be concentrated by evaporation. There can be one or more recycle fractions.

"A sequence" or "a separation sequence" is a predetermined sequence of steps which are continuously repeated in a sequential chromatographic separation process, comprising all steps that are required to facilitate the separation of feed components to product fraction(s) and other fractions. A sequence may include one or more cycles. If a new sequence is started from the same location as the previous sequence, the cycle is equal to the sequence.

"A step" comprises one or more of a feeding phase, an elution phase, and a circulation phase.

During the feeding phase, a feed solution is introduced into a predetermined partial packed bed or predetermined partial packed beds. During the feeding phase, and/or one or more other phases, one or more product fractions and one or more residual fractions can be withdrawn.

During the elution phase, an eluent is fed into predetermined partial packed beds.

During the circulation phase, essentially no feed solution or eluent is supplied to the partial packed beds and no products are withdrawn.

"SMB" refers to a simulated moving bed system.

In a continuous SMB system, all the fluid streams flow continuously.

These streams are: the supply of a feed solution and an eluent, circulation of the separation profile, and withdrawal of the products.

In a sequential SMB system, not all of the fluid streams (defined above) flow continuously.

"A feed" is an amount of feed solution introduced into the separation column during one sequence.

"A subprofile" is a concentration profile of one component, also named as the component peak.

"A separation profile" refers to a dry solids profile formed from the dissolved substances (DS) present in the feed on account of the feed of eluent and feed solution and the flow through the packing material bed in a separation column, obtained by accomplishing/repeating the separation sequence.

"A part of the separation profile" (equal to "part" or "PART") refers to any section of the separation profile which contains liquid and components in this section and which is used as eluent replacement.

"A part feeding phase" refers to the introduction of the part into the separation system as an eluent replacement.

"A peak" is the part of the chromatogram where the detector response is caused by a component.

"A retention volume" (Rt) is the volume of the mobile phase required to elute a component or a certain point of the separation profile through a resin bed. The retention volume of a component may be expressed as % of the resin bed volume. In connection with the present invention, a retention volume especially refers to the volume required to elute the start of a product component fraction (such as a xylose, fructose, betaine or maltose product fraction) through the column.

"Tailing" refers to the phenomenon in which the normal Gaussian peak has an asymmetry factor>1. Tailing is most often caused by sites on the packing that have a stronger than normal retention for the solute.

"A void" or "void volume" in connection with the present invention refers to the volume required to elute the start of the conductivity peak (salts) through the column.

"BV" refers to the resin bed volume of columns, partial packed beds or a separation system.

"Peak broadening" refers to the dispersion of a chromatographic peak (separation profile) as it moves through the column.

"Volume of steps" (V) refers to the volume of the mobile phase (including the feed, eluent and circulation), which moves a component, a separation profile or parts thereof through the separation column(s) from a predetermined step in a separation sequence to another predetermined step in the same or following sequences. The volume of steps is calculated step by step by summing up the volumes of the mobile phase transferred in each step (the volume introduced into the columns in each step during the feeding, elution and/or circulation phases).

"An eluent introduction position" refers to any location in the chromatograhic system where eluent may be introduced.

"DS" refers to the dissolved dry substance content. Equal to "dissolved solids content".

"Purity of a component" refers to the content of the component on DS.

"Separation capacity" refers to the amount of a product (kg of dry solids)/volume of separation resin ($m^3$)/hour (h). Recycle is not included.

"The W/F ratio" refers to the ratio of the volume of eluent water to the volume of the feed.

BRIEF DESCRIPTION OF THE INVENTION

The present invention provides a process for fractionating solutions containing sugars, sugar alcohols, sugar acids and/or betaine in a chromatographic separation system by using parts of the separation profile from the separation as a substitute for the eluent. It is also essential that said parts with their components are directed to a correct position in a correct step in the separation system so that the components contained therein end up into suitable fractions while essentially maintaining or even improving the purity of the product fractions, the yield of the product components and the separation capacity. The objects of the invention are achieved by a process which is characterized by what is stated in the independent claims. Preferred embodiments of the invention are disclosed in the dependent claims.

It was surprising to find out that said parts as a substitute for the eluent and containing different fast moving and/or slow moving components did not disturb the separation efficiency of the separation system. Furthermore, the volume of fresh eluent could be reduced for example in an amount of 10% to 70% from that used in the prior art. The process also provided a higher solids content of the fraction(s) to be withdrawn, which leads to a reduced energy requirement in subsequent concentration stages. The evaporation need for the concentration of residue fractions, for example, may be reduced by an amount of 5 to 50% or even more.

DETAILED DESCRIPTION OF THE INVENTION

The present invention relates to a process for fractionating a solution containing at least one component selected from sugars, sugar alcohols, sugar acids and betaine in a chromatographic separation system, which comprises one or more columns containing one or more partial packed beds, comprising feeding the solution into the separation system, introducing an eluent into the separation system to elute components of the solution to form a separation profile, and recovering one or more product fractions enriched in a product component selected from sugars, sugar alcohols, sugar acids and betaine, one or more residual fractions, and optionally one or more recycle fractions.

The process of the present invention is characterized by introducing one or more parts of the separation profile into one or more eluent introduction positions of the separation system in one or more part feeding phases to substitute a portion of the eluent, said parts comprising one or more components selected from product components and residual components, moving said parts with their components forward in the separation system using a sequence of steps, which steps comprise one or more of a feeding phase, a circulation phase, and an elution phase, and withdrawing components of said parts during the same or following separation sequences in one or more residual fractions and/or in one or more recycle fractions and/or in one or more product fractions, whereby the volume, introduction position and introduction step of said parts are determined on the basis of the retention volumes of the components of said parts, the volume of the resin bed through which the components of the parts pass and the volume of the steps moving the components of the parts from the introduction position to the calculated target withdrawal position of the components during said same or following separation sequences while essentially maintaining or improving the purity of the product fraction(s) and the yield of the product components.

The chromatographic separation system of the present invention comprises one or more separation columns containing one or more partial packed beds. The partial packed beds are composed of a chromatographic separation resin, which forms the resin bed of the system. The columns/partial packed beds may form one or more loops. During the separation process, the dissolved substances present in the feed, together with the eluent, are moved forward and separated in the partial packed beds of the separation column(s), resulting in the formation of a separation profile. One or more product fractions, one or more residual fractions and also generally one or more recycle fractions are recovered.

In the process of the present invention, one or more parts of the separation profile thus formed are introduced into one or more eluent introduction positions in one or more part feeding phases to substitute a portion of the eluent. Said parts may be introduced to substitute the eluent at the beginning, in the middle or at the end of an elution phase.

In the following description of the invention, for the sake of convenience, said one or more parts of the separation profile are also referred to as "parts of the separation profile" or "parts".

Said parts may be introduced into any column or any part of a column whereto an eluent is introduced.

In the process of the invention, the product components may be selected from sugars, sugar alcohols, sugar acids, and betaine.

The sugars may be selected from xylose, fructose, glucose, mannose, arabinose, galactose, rhamnose, fucose, sucrose, maltose, levoglucosan, ribose, isomaltulose, tagatose, trehalose, trehalulose, and psicose.

In connection with the present invention, sugars also comprise oligomeric compounds, such as malto-oligosaccharides, fructo-oligosaccharides, and polydextrose.

The sugar alcohols may be selected from xylitol, mannitol, sorbitol, inositol, maltitol, isomalt, and erythritol.

The sugar acids may be selected from hydroxy acids, carboxylic acids, such as aldonic acids, e.g. xylonic acid, gluconic acid, and itaconic acid, and uronic acids, such as glucuronic acid and galacturonic acid, for example, Especially preferred product components in connection with the present invention are xylose, fructose, maltose and betaine.

The residual components are typically selected from salts, organic acids, for example acetic acid, and inorganic acids and salts thereof, e.g. sulfuric acid and sulfurous acid, amino acids, color compounds, glycerol, lignosulfonates, oligosaccharides, etc., depending on the starting material as well as to sugars, sugar alcohols and sugar acids other than the product sugars, sugar alcohols, and sugar acids.

For example, in the separation of sugars, sugar alcohols, and sugar acids from plant-based hydrolysates, such as sulfite spent liquor, the residual components mainly comprise lignosulfonates, oligosaccharides, salts, organic acids (e.g. xylonic acid), and inorganic acids (e.g. acetic acid), etc. In the separation of fructose from mixtures of glucose and fructose, such as inverted sucrose and isomerized glucose, the residual components mainly comprise e.g. disaccharides and glucose. In the separation of betaine from sugar-beet based solutions, such as molasses and vinasse, the residual components mainly comprise salts, color compounds, organic acids, amino acids, glycerol, and mono-, di- and trisaccharides, etc. in the separation of cane molasses, the residual components mainly comprise salts, color compounds, mono-, di- and trisaccharides. In the separation of maltose from starch hydrolysates, the residual components mainly comprise oligomers, glucose, and maltotriose.

The starting materials containing one or more product components selected from sugars, sugar alcohols, sugar acids, and betaine are typically multicomponent plant-based extracts and hydrolysates or derivatives thereof. Sulfite spent liquor, starch hydrolysate, and sugar beet based solutions, such as molasses, stillages and fermentation products thereof, such as vinasse, can be mentioned as examples of suitable starting materials.

One embodiment of the invention comprises the separation of sugars, sugar alcohols, and sugar acids from plant-based hydrolysates, plant-based extracts and derivatives thereof. The plant-based hydrolysates may be obtained from vegetable material, including wood material from various wood species, particularly hardwood, such as birch, aspen and beech, maple, eucalyptus, various parts of grain (such as straw, especially wheat straw, husks, particularly corn and barley husks and corn cobs and corn fibers), bagasse, cocoanut shells, cottonseed skins, almond shells, etc. The plant-based extracts may be for example water, vapour, alkaline or alcohol extracts of the plants described above. Derivatives of plant-based hydrolysates and extracts may be different post-treated products, such as evaporation products thereof or fractions from membrane processes.

In one specific embodiment of the invention, the plant-based hydrolysate for the separation of sugars, sugar alcohols, and sugar acids, such as xylose, is a spent liquor obtained from a pulping process. A typical spent liquor useful in the present invention is a spent sulfite pulping liquor, which is preferably obtained from acid sulfite pulping. One example of a useful hydrolysate is a prehydrolysate from sulfate pulping.

In a further specific embodiment, xylose is separated from a xylose run-off obtained from the crystallization of xylose. In a further specific example of the invention, xylitol is separated from a xylitol run-off after hydrogenation of xylose and crystallization of xylitol.

In a further specific embodiment, xylitol or erythritol is separated from fermentation broths.

Another embodiment of the invention comprises the separation of fructose from mixtures of glucose and fructose, such as solutions of inverted sucrose, solutions of isomerized glucose and mixtures thereof as well as run-offs obtained from the crystallization of fructose.

A further embodiment of the invention comprises the separation of maltose from starch hydrolysates, such as maltose syrups. A still further embodiment of the invention comprises the separation of maltitol from a maltitol syrup after hydrogenation of maltose.

A still further embodiment of the invention comprises the separation of betaine from a sugar beet based solution, such as molasses and vinasse.

Said parts of the separation profile used as an eluent replacement in the process of the invention may comprise one or more components selected from product components and residual components.

Said parts may contain fast-moving and/or slow-moving components. Salts, organic acids, and inorganic acids represent an example of the fast-moving components.

Said parts may be front and/or rear slopes of the subprofiles of the product components or residual components. Said parts are typically front slope and/or rear slope portions of a subprofile of the product components, and one or more different front slope portions of a residual subprofile.

In the process of the present invention, said parts with their components are moved forward in the separation system by using a sequence of steps, which steps comprise one or more of a feeding phase, a circulation phase, and an elution phase.

In the sequential separation system, several of said parts originating from different parts of the separation profile may be used as an eluent during one sequence. The number of said parts may be 1 to 5, and they may be introduced as an eluent into various positions of the system either as collected fractions or transferred as an intact profile.

Withdrawal of components of said parts during the same or following separation sequences may be carried out in residual fraction(s), recycle fraction(s) and/or product fraction(s) directly or after an intermediate stage.

Moving of the components of said parts in the separation system may proceed through intermediate stages before the final withdrawal thereof. Intermediate stages are untypical fractions or positions in the separation profile, where the component(s) is/are directed to be reintroduced back to the separation system for the final separation and withdrawal thereof or to be reintroduced into a distinct separation system.

The components of said parts are typically withdrawn during the same or following separation sequences in the zone of one or more residual fractions or directed either to a recycle fraction or circulated in a circulation phase to be introduced back into the system to be finally withdrawn in the zone of one or more residual fractions. For example, betaine of said parts is typically directed to a sucrose recycle fraction to be added to dilute a feed solution and to increase the betaine content of the feed and to be withdrawn in a final betaine fraction.

In another example relating to the separation of xylose, the parts containing residual components, such as lignosulfonates and salts, may be essentially or partially directed to a recycle fraction, followed by withdrawing the residual components essentially in a residual fraction during the following 1 to 4 separation sequences.

In a further example relating to the separation of fructose, the parts containing residual components, such as disaccharides and glucose may be essentially or partially directed to a recycle fraction, followed by withdrawing the residual components essentially in a residual fraction during the following 1 to 4 separation sequences.

The volume, introduction position and introduction step of said parts are determined on the basis of the retention volumes of the components of said parts, the volume of the resin bed through which components of the parts pass and the volume of the steps moving the components of said parts from the introduction position to the calculated target withdrawal position of the components during said same or following separation sequences while essentially maintaining the purity of the product fraction(s) and the yield of the product components, It is essential that the volume, introduction position and introduction step of said parts are determined to be suitable an that the components of said parts at the withdrawal thereof either reach the region of the similar fast moving components of the feed or are retained to be eluted together with the faster moving components of the feed or they allow the fast moving components of the separation profile to reach the slow moving components of said parts.

The volume, introduction position and introduction step of said parts are determined by first determining the target fraction or fractions and their volumes as well as the column(s) and step(s) in which the component(s) of said parts are to be withdrawn. For example, if the main component of said parts is betaine and/or sucrose, the betaine/sucrose component is to be withdrawn in some of the recycle fractions of another product component (e.g. betaine is withdrawn in a sucrose recycle fraction) which are withdrawn from predetermined columns in predetermined steps of the process. The sucrose recycle fraction may be e.g. a front slope part or a rear slope part of a sucrose subprofile. These recycle fractions are then recycled back to the feed solution for further separation and for further recovery of betaine/sucrose. If the main components of said parts are residual components, such as salts, the salt components are to be withdrawn in some of the zones of the residue fractions to be withdrawn from predetermined columns in predetermined steps of the process during the next or following sequences.

The retention volumes of the components of said parts for each separation system are experimentally determined for the resin beds in use.

For example in the separation of xylose from sulfite spent liquor, the retention volume of xylose is approximately 60% (between 57 and 63%) of the resin bed volume used for divalent strong acid cation exchange resin beds (a magnesium form resin having a DVB content of 6 to 6.5%). The retention volume of the start of the conductivity peak (salts and large molecules, such as lignosulfonates) in the same sulfite spent liquor separation with the same resins is approximately 33% of the resin bed volume, which is equal to the void volume of the resin bed. Also the peak broadening phenomenon must be taken into account when calculating the elution volumes, in which different components are eluted from the separation column.

In the separation of fructose and glucose from inverted sucrose, the retention volume of fructose is approximately 72% (between 69 and 75%) and the retention volume of glucose is approximately 52% (between 47 and 55%) of the resin bed volume used for divalent strong acid cation exchange resin beds (calcium form resin having a DVB content of approximately 5.5%). The retention volume of the start of the separation profile (large molecules, such as disaccharides) in the same inverted sugar separation with the same resins is approximately 40% (between 38 and 45%) of the resin bed volume.

In the separation of maltose from starch hydrolysate, the retention volume of maltose is approximately 52% (between 49 and 55%) of the resin bed volume used for monovalent strong acid cation exchange resin beds (a sodium form resin having a DVB content of approximately 5.5%). The retention volume of the start of the separation profile (large molecules, such as oligosaccharides) in the same starch hydrolysate separation with the same resins is approximately 33% of the resin bed volume.

In the separation of betaine and glycerol from vinasse, the glycerol fraction is advantageously introduced into a suitable position of the separation system in the elution of the next feed or feeds (sequences) as an eluent replacement. Glycerol is then withdrawn in a residual fraction simultaneously with fast moving components (such as salts). This is achieved by utilizing the differences in the retention volumes of salts and glycerol. The retention volume of salts for strongly acid cation exchange beds is approximately 27 to 34% of the resin bed volume and the retention volume of glycerol is approximately 65 to 75% of the resin bed volume.

In the separation of beet molasses, the retention volume of betaine is approximately 70% (between 67 and 73%) of the resin bed volume used and the retention volume of sucrose is approximately between 55% and 60% of the resin bed volume used for monovalent strong acid cation exchange resin beds (having a DVB content of 6 to 6.5%). The retention volume of the start of the conductivity peak (salts and large molecules) in the same molasses separation with the same resins is approximately between 28 and 34% of the resin bed volume, which is equal to the void volume of the resin bed.

The movement of different components (such as sugars, betaine and salts) of said parts in the separation process, such as in a sequential SMB system, during one sequence and especially during the following 1 to 4 sequences can then be calculated on the basis of the retention volumes (Rt) of the components, the volume of the resin bed (BV) through which the components of the parts pass and the volume of the steps (V) moving the components of said parts during said sequences (calculated step by step). A component starts eluting from the separation system (column) when the volume of the steps moved through the system is equal to the retention volume of the component in question. This determines the target withdrawal position of the component concerned. When the target withdrawal position is known, the introduction volume, position and step of said parts as an eluent substituent can then be calculated upstream step by step so that the components of said parts end up and are withdrawn in the target fractions essentially during the following 1 to 4 sequences. This is achieved when the volume of the steps from the target withdrawal position to the introduction position of said parts is equal to the retention volume of the components of said parts through the resin bed from introduction to withdrawal. The volume of steps is calculated upstream from column to column step by step by summing up the volumes introduced into the columns in each step during the feeding, elution, and circulation phases, starting with the target position.

The volumes of the parts as flow rates ($m^3/h$) may be measured either from the inlet or outlet of the columns.

The desired components are withdrawn during said same or following separation sequences in one embodiment of the invention, the desired components are essentially withdrawn during the following 1 to 4 separation sequences.

The chromatographic separation system may be a batch system or an SMB system, which may be continuous or sequential.

In a preferred embodiment of the invention, the chromatographic separation system is a sequential SMB system described in U.S. Pat. Nos. 6,093,326, 5,127,957, 6,572,775, and 6,896,811.

The sequential chromatographic SMB system may contain one or more loops in the system. The system may also contain one or more separation profiles in a loop.

In one embodiment of the invention, the separation profile is circulated more than once or less than once through the resin bed of the system during one cycle.

The chromatographic separation resins in the partial packed beds of the separation system may be selected from those commonly used for the separation of the above-described product components from multicomponent to plant-based extracts and hydrolysates and derivatives thereof. Especially useful resins are strongly acid cation exchange resins (SAC) and weakly acid cation exchange resins (WAC), but even weakly basic anion exchange resins (WBA) and strongly basic anion exchange resins (SBA) can be used. The cation exchange resins (SAC and WAC) may be in monovalent, divalent or trivalent form, such as in $H^+$, $Na^+$, $K^+$, $Ca^{2+}$, $Mg^{2+}$, $Zn^{2+}$, $Sr^{2+}$, $Ba^{2+}$ or $Al^{3+}$ form.

The resins may be styrenic or acrylic resins having a crosslinking degree in a range of 1 to 20%, for example 4 to 10% DVB (divinylbenzene), The crosslinking degree of the resins as a rule affects the retention volume of the components. A typical mean particle size of the resins is 200 to 450 μm.

The dry solids content of said parts used as an eluent replacement is typically 0.2 to 50%, preferably 1 to 30%.

The dry solids content of the parts is typically 3 to 30% when the feed solution is a sulfite spent liquor, which has a dry solids content e.g. of 25 to 55%. The xylose content of said parts may be in a range of 0 to 75% on DS, preferably in a range of 0 to 15% on DS.

The dry solids content of the parts is typically 0.2 to 15% when the feed solution is sugar beet molasses, which has a dry solids content e.g. of 30 to 60%. The betaine content of said parts may be up to 80% on DS.

The dry solids content of the parts is typically 0.2% to 25%, preferably in a range of 0.2 to 10%, when the feed solution is inverted sucrose or isomerized glucose. The fructose content of said parts may be in a range of 0 to 95% on DS, preferably in a range of 0 to 10% on DS.

The dry solids content of the parts is typically 0.2 to 25%, preferably in a range of 0.2 to 10% when the feed solution is a starch hydrolysate. The maltose content of the parts may be in a range of 0 to 95% on DS, preferably in a range of 0 to 25% on DS.

In one embodiment of the invention, said one or more parts are front slope parts or rear slope parts of a first product component subprofile, which posses a high content of a first product component. This embodiment of the invention comprises introducing said front slope parts and/or rear slope parts of the first product component subprofile back into said separation system to replace a portion of the eluent water, followed by withdrawing the first product component of said front slope or rear slope parts during the next sequence in a recycle fraction of a second product component. The recycle fraction is recycled to the feed for further separation of the first product component. The first to product component from slopes is finally recovered in the first product component fraction, which has a higher dry solids concentration and may also have a higher content of the first product component than without circulation of the slopes.

In one embodiment of the invention, the first product component is betaine and the second product component is sucrose. The front and rear slope parts of a betaine subprofile as the first product component subprofile have typically a dry solids concentration of 0.2% to 8%, and the betaine content of the betaine subprofile is up to 80% on dry solids (DS).

In another embodiment of the invention, said one or more parts may be selected from front slope parts and rear slope parts of a residual subprofile. In this embodiment of the process of the invention, said front slope parts or rear slope parts of a residual subprofile are introduced back into said separation system to replace a portion of the eluent water, the components thereof are moved to the region of other residual components, followed by withdrawing the residual components of said slope parts in more than one residual fraction during the same or following 1 to 4 sequences.

In one embodiment of the invention, the front slope and/or rear slope of the residual subprofile may be divided into several subsections, which are introduced into the separation system as an eluent replacement. It is also possible to circulate only some of the subsections as an eluent replacement, while some of them are withdrawn from the system. Selection of a subsection for an eluent replacement will be done according to its volume and its introduction (column and step) and withdrawal positions based on the knowledge on its retention volume in the separation. Subsections for eluent replacement can be selected from the more dilute end, the middle or the most concentrated part of the residual fraction.

In one embodiment of the invention, the front slope of the residual subprofile may be divided for example into four subsections (sections 1 to 4), whereby sections 1 and 3 are withdrawn from the separation system and sections 2 and 4 are used as an eluent replacement by introducing them in calculated steps to different columns intermittently.

In a further embodiment of the invention, said one or more parts may be selected from front slope parts and rear slope parts of a second product component subprofile. This embodiment of the invention comprises introducing said front slope parts or rear slope parts of a second product component subprofile back to said separation system to replace a portion of the eluent water, followed by withdrawing the second product component of said front slope or rear slope parts during the next sequence in a recycle fraction. The recycle fraction is recycled to the feed for further separation of the second product component. The second product component is finally recovered in a fraction of the second product component.

In a still further embodiment of the invention, said one or more parts may comprise both (1) one or more parts of a product component subprofile, such as front slope parts and/or rear slope parts of a product component subprofile, and (2) one or more parts of the residual subprofile. Different parts may be combined or introduced separately to different eluent introduction positions to enable the withdrawal of the components of the parts in suitable fractions during the same or following sequences.

The volume of said part is preferably less than that of the recycle fraction or residue fraction in which the components of said parts are to be withdrawn.

In one embodiment of the invention, said parts are introduced into the separation system as an intact separation profile as a continuous stream from another column.

In another embodiment of the invention, said parts are collected into a separate tank and introduced back into the separation system from the tank.

The total volume of said parts used for an eluent replacement in the separation system is 1 to 50%, advantageously 5 to 20%, of the volume of all steps moving the separation profile forward during one separation sequence.

Said parts are typically used for substituting 5 to 70%, preferably 10 to 30%, of eluent water. The amount of the replacement eluent is preferably the same as that of the omitted water eluent.

In a typical embodiment of the invention, the process provides a product component fraction where the content of the product component is 35 to 99% on DS.

In a specific embodiment of the invention, the process provides a betaine product fraction with a betaine content of 40 to 98%, preferably 60 to 90%, on DS. In another specific embodiment of the invention, the process provides a xylose product fraction with a xylose content of 35 to 80%, preferably 40 to 75%, on DS. In a further specific embodiment of the invention, the process provides a fructose product fraction with a fructose content of 85 to 99%, preferably 90 to 98%, on DS. In a still further specific embodiment of the invention, the process provides a maltose product fraction with a maltose content of 85 to 99%, preferably 90 to 98%, on DS.

In a typical embodiment of the invention, the process provides a product component yield in a range of 60 to 98% based on the product component in the feed solution.

In a specific embodiment of the invention, the process provides a betaine yield of more than 60%, preferably more than 70%, more preferably more than 80%, most preferably more than 85%, and especially more than 90%, based on the content of betaine in the feed solution. In a further specific embodiment of the invention, the process provides a xylose, fructose or maltose yield of more than 85%, preferably more than 90%, and more preferably more than 95%, based on the content of xylose, fructose or maltose in the feed solution.

In one specific embodiment of the invention, sulfite spent liquor is separated using a 5-column chromatographic system with a mode according to U.S. Pat. No. 5,637,225 to provide a xylose fraction, a recycle fraction, and a residual fraction. The residual fraction contains fast moving components, such as lignosulfonates and salts, and the aim is to re-use a part of a residual fraction as an eluent replacement and recover these components to other residual fractions, which are normally eluted from the system. The part is taken from the front of a separation profile in the last columns (e.g. from columns 4 and 5 in a 5-column system) and is introduced back to the first columns of the separation system (e.g. to columns 1 and 3 in a 5-column system) to substitute eluent water. The part from column 5 can be directly introduced into column 1 as an eluent replacement and the part from column 4 can be collected into a collecting tank and introduced as a mixed solution to column 3 also as an eluent replacement. In this specific embodiment, parts were replacing the last portion of the water feed into a column. The volume of the part must not be too large to fit into the desired withdrawal region. The components of the part have to be able to pass the slower moving components of the whole separation profile of the feed without disturbing their separation and reaching a region where lignosulfonates and salts are located and overlapping the region. The components of the part (lignosulfonates and salts) can be recovered into at least one residual fraction in a more concentrated form than without using the part and be removed from the system. The part with its components can be divided into separate streams (leading to different columns) in the system and be partly recovered also either in a recycling fraction to be added to the feed solution for dilution or before concentration or in a fraction to be reused as an eluent. The volume of the required total fresh eluent is at least 20% lower, preferably over 40% lower, than without using of part.

In another specific embodiment of the separation of molasses, front slope parts and rear slope parts of a betaine subprofile (which have a high betaine purity, but a low dry substance content) are introduced back into the separation system as an eluent replacement. The introduction position and volume of said betaine-containing front slope parts and rear slope parts as an eluent substitute are calculated so that the betaine in said parts during the separation process moves to the sucrose recycle fraction. Said parts containing the slow-moving betaine are thus introduced into such a position that the residual components (salts) of the separation profile pass betaine of the parts and the new peak of the betaine from the parts will be within the collection interval of the sucrose recycle fraction. The recycle fraction is collected at a point where sucrose and residual components (salts) partly overlap. In this process, betaine can be efficiently recovered from the dilute betaine-containing front slope parts and rear slope parts of a betaine subprofile. Consequently, the concentration (dry substance and betaine) of the betaine product fraction rises and the water in the dilute betaine-containing front slope parts and rear slope parts is utilized as an eluent.

In a further embodiment relating to the separation of fructose from a fructose-containing solution, such as a fructose run-off, parts containing disaccharides and glucose (parts of the residue fraction) are introduced back to the separation system as an eluent. Disaccharides and glucose ere than withdrawn during the following 1 to 4 separation sequences in residue fractions.

In a still further embodiment relating to the separation of maltose from a starch hydrolysate, parts containing oligosaccharides and glucose (parts of the residue fraction) are introduced back to the separation system as an eluent replacement. Oligosaccharides and glucose are then withdrawn during the following 1 to 4 sequences in residue fractions.

In a further specific embodiment of the invention relating to the chromatographic separation of vinasse with SAC resin in $Na^+$ form and WAC resin in $H^+$ form (DVB content 8%), the elution order is salts (the most fast-moving component), glycerol, and betaine (the slowest component). In one embodiment of the invention, the glycerol-containing fraction obtained from the separation with the WAC resin is introduced back to the separation system to replace a portion of the eluent water in the elution of the next feed in a suitable position by calculating the introduction volume and step of the glycerol fraction so that glycerol moves in the separation profile during the next feed or feeds (sequences) to be withdrawn from the system in the salt-glycerol fraction.

Furthermore, it has been discovered that the invention can be utilized for example in a sequential SMB separation system comprising a two-loop configuration according to U.S. Pat. No. 5,637,225 or U.S. Pat. No. 6,093,326. A part, which has advantageously a dry solids content of 3 to 30% and comprises a mixture of feed components moving faster or slower than the main product components, may be taken from the second loop and can be used to replace a substantial amount (15 to 50%) of fresh eluent by introducing the part to the first loop into the column(s) between the separation profiles and allowing the part to act as an eluent. A portion of the part with its components and a part of the separation profile which overlaps with the part are recovered in more than one withdrawn fraction, e.g. residual fractions, from various columns in the first loop during the following through-passages in the first loop. The concentration of the components of the part (g/l) in the collected residual fractions is higher than without using the part.

In sequential SMB, the use of the parts as an eluent can be implemented in different ways, for example as follows:

performing the previously used circulation phase longer (moving larger volumes forward) for example in the sequential SMB system of U.S. Pat. Nos. 5,127,957, 5,637,225 or 6,093,326, thus allowing the part (containing e.g. salts) to enter a column and to act as an eluent and recovering salts of the part together with the salts of the feed in a residual fraction (containing salts of the feed) from columns in a normal way, or performing an extra step in a sequential SMB system comprising five columns, where a previously withdrawn residual fraction (comprising either faster or slower moving components than the product component) from column 4 or 5 is introduced either as an undisturbed part of the profile or as a separate part feed from a collecting tank or container into a column depending on the components of the part and the desired outlet fraction for the part components. The part from column 5 may be directly introduced into column 1 as an eluent replacement and the part from column 4 can be collected into a collecting tank and introduced as a mixed solution into columns 2 and 3 also as an eluent replacement. When the part is introduced into a column, it can replace a portion or all of the eluent feed into one column in one step. It can be advantageous to is replace the last portion of the eluent feed into a column and allow separation profile in a next step to follow the introduced part immediately after the introduction step.

In the process of the present invention, said one or more parts of the separation profile are typically utilized as an eluent replacement within the same separation system. However, it is also possible to introduce said parts as an eluent replacement to other similar parallel separation systems or to different separation systems.

The following examples illustrate the invention without limiting the invention in any way.

EXAMPLE 1

Chromatographic SMB Separation of MySSL®—Reference Example

The process equipment included five columns connected in series, a feed pump, recycling pumps, an eluent water pump, heat exchangers, flow control means for out-coming liquids as well as inlet and product valves for the various process streams. The height of first three columns was 3.6 m and the height of last two columns was 4.6 m, and each column had a diameter of 4.2 m. The columns were packed with a strong acid gel type cation exchange resin (manufactured by Finex) in $Mg^{2+}$ form. The divinylbenzene content of the resin was 6.5%, and the mean bead size of the resin was 0.38 mm.

Before the separation, $Mg^{2+}$ sulfite spent liquor (MgSSL) was diluted with a recycle fraction to 52 weight-% and pre-coat filtered using Arbocel B800 as a filter aid. The feed dry substance was further adjusted with a recycle fraction to 48.1 g/100 g and the feed liquor pH was 3.4. The feed was composed as set forth below, whereby the percentages are given on a dry substance weight basis.

TABLE E1-1

| Composition of the feed, % on DS | |
|---|---|
| Glucose | 2.2 |
| Xylose | 17.2 |
| Galactose + rhamnose | 1.6 |
| Arabinose + mannose | 1.8 |
| Xylonic acid | 5.6 |
| Others (mostly salts) | 26.2 |
| Lignosulfonates | 45.4 |

The fractionation was performed by way of a 9-step SMB sequence as set forth below. The aim of the separation was to separate xylose contained therein. The feed and the eluent were used at a temperature of 70° C., and the condensate from residual and xylose fraction evaporations was used as an eluent.

Step 1: 4.8 $m^3$ of feed solution was pumped into the first column at a flow rate of 90 $m^3$/h, and a recycle fraction was collected from the third column. Simultaneously, 2.0 $m^3$ was circulated in the column loop, formed with columns 4 and 5, at a flow rate of 45 $m^3$/h.

Step 2: 9.5 $m^3$ of feed solution was pumped into the first column at a flow rate of 95 $m^3$/h, and a residual fraction was collected from the same column. Simultaneously, 8.1 $m^3$ of eluent was pumped into the second column at a flow rate of 85 $m^3$/h, and first, 6.6 $m^3$ of recycle fraction and than 1.5 $m^3$ of xylose fraction were collected from the last column.

Step 3: 6.4 $m^3$ of feed solution was pumped into the first column at a flow rate of 65 $m^3$/h, and a xylose fraction was collected from the last column.

Step 4: 10.8 $m^3$ of feed solution was pumped into the first column at a flow rate of 65 $m^3$/h, and a residual fraction was collected from the fourth column. Simultaneously, 12.7 $m^3$ of eluent was pumped into the last column at a flow rate of 95 $m^3$/h, and first, 10.2 $m^3$ of xylose fraction and then 2.5 $m^3$ of recycle fraction was collected from the same column.

Step 5: 1.0 $m^3$ of feed solution was pumped into the first column at a flow rate of 70 $m^3$/h, and a residual fraction was collected from the second column. Column 3 was waiting for the next step. Simultaneously, 21.0 $m^3$ circulation was started in the column loop, formed with columns 4 and 5, at a flow rate of 55 $m^3$/h.

Step 6: 11.5 $m^3$ of eluent was pumped into the third column at a flow rate of 70 $m^3$/h, and a residual fraction was collected from the second column. Simultaneously, circulation in the column loop, formed with columns 4 and 5, was continued at a flow rate of 55 $m^3$/11, Step 7: 17.2 $m^3$ was circulated in the column loop, formed with columns 1, 2 and 3, at a flow rate of 75 $m^3$/h. Simultaneously, circulation in the column loop, formed with columns 4 and 5, was continued at a flow rate of 55 $m^3$/h.

Step 8: 11.6 $m^3$ of eluent was pumped into the first column at a flow rate of 80 $m^3$/h, and a residual fraction was collected from the third column. Simultaneously, 10.6 $m^3$ of eluent was pumped into the fourth column at a flow rate of 60 $m^3$/h, and a residual fraction was collected from the last column.

Step 9: 11.9 $m^3$ was circulated in the column loop, formed with columns 1, 2 and 3, at a flow rate of 95 $m^3$/h. Simultaneously, 6.0 $m^3$ was circulated in the column loop, formed with columns 4 and 5, at a flow rate of 60 $m^3$/h.

After equilibration of the system, the following fractions were drawn from the system: a residual fraction from each column, recycle fractions from the third and fifth column, and xylose product fractions from the last column. The results, including HPLC analyses for the combined fractions and for column 5 residual, are set forth in the table below.

TABLE E1-2

|  | Combined Residual | Combined recycle | Combined xylose | Column 5 residual | Column 1 residual |
|---|---|---|---|---|---|
| Volume, m$^3$ | 55.0 | 13.9 | 18.1 | 10.6 | 9.5 |
| Dry solids, weight-% | 18.8 | 25.7 | 25.1 | 14.5 | 20.7 |
| Dry solids, g/100 ml | 20.4 | 29.2 | 27.7 | 15.4 | 22.5 |
| Glucose, % on DS | 0.5 | 4.0 | 4.6 | 1.4 | 0.2 |
| Xylose, % on DS | 1.2 | 24.2 | 46.1 | 3.8 | 0.2 |
| Galactose + rhamnose, % on DS | 0.1 | 2.5 | 4.1 | 0.4 | 0.0 |
| Arabinose + mannose, % on DS | 0.2 | 2.7 | 4.6 | 0.6 | 0.1 |
| Xylonic acid, % on DS | 3.7 | 5.0 | 8.5 | 6.8 | 1.6 |
| Lignosulfonates, % on DS | 58.8 | 19.4 | 5.8 | 41.5 | 66.4 |
| Others (mostly salts), % on DS | 35.5 | 42.2 | 26.3 | 45.5 | 31.5 |

The overall xylose yield calculated from these fractions was 94.5%. In the reference run, all residual was taken out from the system and the W/F (water to feed) ratio was 1.7. When the residual fraction is evaporated to 60 weight-%, the condensate removal is 41.0 tons per separation cycle.

EXAMPLE 2

Chromatographic SMB Separation of MgSSL

The process equipment included five columns connected in series, a feed pump, recycling pumps, an eluent water pump, heat exchangers, flow control means for out-coming liquids as well as inlet and product valves for the various process streams. The height of first three columns (a volume of 49.9 m$^3$ each) was 3.6 m and the height of last two columns (a volume of 63.7 m$^3$ each) was 4.6 m, and each column had a diameter of 4.2 m. The columns were packed with a strong acid gel type cation exchange resin (manufactured by Finex) in Mg$^{2+}$ form. The divinylbenzene content of the resin was 6.5%, and the mean bead size of the resin was 0.38 mm.

Before the separation. Mg$^{2+}$ sulfite spent liquor was diluted with a recycle fraction to 52 weight-% and pre-coat filtered using Arbocel B800 as a filter aid. The feed dry substance was further adjusted with a recycle fraction to 48.2 g/100 g, and the feed liquor pH was 3.22. The feed was composed as set forth below, whereby the percentages are given on a dry substance weight basis.

TABLE E2-1

| Composition of the feed, % on DS | |
|---|---|
| Glucose | 2.3 |
| Xylose | 17.8 |
| Galactose + rhamnose | 1.7 |
| Arabinose + mannose | 1.8 |
| Xylonic acid | 5.3 |
| Others (mostly salts) | 25.5 |
| Lignosulfonates | 45.3 |

The fractionation was performed by way of a 10-step SMB sequence as set forth below. The aim of the separation was to separate xylose contained therein. The feed and the eluent were used at a temperature of 70° C. and the condensate from residual and xylose fraction evaporations was used as an eluent.

Step 1: 4.8 m$^3$ of feed solution was pumped into the first column at a flow rate of 90 m$^3$/h, and a recycle fraction was collected from the third column, Simultaneously, 2.0 m$^3$ was circulated in the column loop, formed with columns 4 and 5, at a flow rate of 45 m$^3$/h.

Step 2: 9.5 m$^3$ of feed solution was pumped into the first column at a flow rate of 95 m$^3$/h, and a residual fraction was collected from the same column. Simultaneously, 8.1 m$^3$ of eluent was pumped into the second column at a flow rate of 85 m$^3$/h, and first, 6.6 m$^3$ of recycle fraction and then 1.5 m$^3$ of xylose fraction was collected from the fifth column.

Step 3: 6.4 m$^3$ of feed solution was pumped into the first column at a flow rate of 65 m$^3$/h, and a xylose fraction was collected from the fifth column.

Step 4: 10.8 m$^3$ of feed solution was pumped into the first column at a flow rate of 65 m$^3$/h, and a residual fraction was collected from the fourth column. Simultaneously, 12.7 m$^3$ of eluent was pumped into the fifth column at a flow rate of 95 m$^3$/h, and first, 10.2 m$^3$ of xylose fraction and then 2.5 m$^3$ of recycle fraction was collected from the fifth column.

Step 5: 1.0 m$^3$ of feed solution was pumped into the first column at a flow rate of 70 m$^3$/h, and a residual fraction was collected from the second column. Column 3 was waiting for the next step. Simultaneously, 21.0 m$^3$ circulation was started in the column loop, formed with columns 4 and 5, at a flow rate of 55 m$^3$/h.

Step 6: 11.5 m$^3$ of eluent was pumped into the third column at a flow rate of 70 m$^3$/h, and a residual fraction was collected from the second column. Simultaneously, circulation in the column loop, formed with columns 4 and 5, was continued at a flow rate of 55 m$^3$/h.

Step 7: 17.2 m$^3$ was circulated in the column loop, formed with columns 1, 2 and 3, at a flow rate of 75 m$^3$/h. Simultaneously, circulation in the column loop, formed with columns 4 and 5, was continued at a flow rate of 55 m$^3$/h.

Step 8: 2.6 m$^3$ of eluent was pumped into the first column at a flow rate of 80 m$^3$/h, and a residual fraction was collected from the third column. Simultaneously, 1.6 m$^3$ of eluent was pumped into the fourth column at a flow rate of 60 m$^3$/h, and a residual fraction was collected from the last column.

Step 9: 9.0 m$^3$ of eluent was pumped into the fourth column at a flow rate of 90 m$^3$/h, and a residual fraction was collected from the third column in an open loop of all columns. Simultaneously, the residual fraction from column 5 (PART) was introduced into column 1 to act as an eluent.

Step 10: 11.9 m$^3$ was circulated in the column loop, formed with columns 1, 2 and 3, at a flow rate of 95 m$^3$/h. Simultaneously, 6.0 m$^3$ was circulated in the column loop, formed with columns 4 and 5, at a flow rate of 60 m$^3$/h.

After equilibration of the system, the following fractions were drawn from the system: a residual fraction from each column, recycle fractions from the third and fifth column, and xylose product fractions from the last column. The results, including HPLC analyses for the combined fractions, are set forth in the table below.

TABLE E2-2

|  | Combined Residual | Combined recycle | Combined xylose | Column 5 residual | Column 1 residual |
|---|---|---|---|---|---|
| Volume, m$^3$ | 46.0 | 13.9 | 18.1 | 1.6 | 9.5 |
| Dry solids, weight-% | 22.1 | 27.3 | 25.7 | 13.6 | 26.5 |
| Dry solids, g/100 ml | 24.4 | 31.1 | 28.4 | 14.3 | 29.7 |
| Glucose, % on DS | 0.6 | 3.8 | 4.5 | 0.1 | 0.5 |
| Xylose, % on DS | 1.2 | 23.0 | 45.6 | 4.0 | 0.9 |
| Galactose + rhamnose, % on DS | 0.1 | 2.3 | 4.1 | 0.3 | 0.1 |
| Arabinose + mannose, % on DS | 0.2 | 2.4 | 4.3 | 0.4 | 0.2 |
| Xylonic acid, % on DS | 3.6 | 5.0 | 8.5 | 12.3 | 4.5 |
| Lignosulfonates, % on DS | 60.4 | 29.4 | 6.9 | 38.6 | 59.5 |
| Others (mostly salts), % on DS | 33.9 | 34.1 | 26.1 | 44.3 | 34.3 |

The overall xylose yield calculated from these fractions was 94.6%. In the test run, 9.0 m$^3$ of column 5 residual was introduced into the first column in step 9, and the W/F (water to feed) ratio was 1.40 compared to 1.7 in the reference run (Example 1). When the residual fraction is evaporated to 60 weight-%, the condensate removal is 32.1 tons per separation cycle, and the residual fraction evaporation demand was reduced 22% as compared with the reference test run.

A simplified calculation of the movement of the PART (e.g. the residual fraction from column 5) and its components was done assuming that the void volume is 33% of the bed volume and lignosulfonates and salts have no retention on the resin. By comparing the analysis of Residual 5 and Residual 1 to the reference run, it can be calculated that for example xylonic acid from residual 5 introduced into column 1 is mainly eluted already in the next Residual 1 on account of the xylonic acid retention.

EXAMPLE 3

Chromatographic SMB Separation of MgSSL—Pilot Test

The process equipment included five columns connected in series, a feed pump, recycling pumps, an eluent water pump, heat exchangers, flow control means for out-coming liquids as well as inlet and product valves for the various process streams. The equipment also included a tank, a feed pump, lines, flow control means and valves for the collection and feeding of a fraction to be used as an eluent water replacement. The height of first three columns (a volume of 282 liters each) was 3.6 m, and the height of last two columns (a volume of 36.1 liters each) was 4.6 m, and each column had a diameter of 0.11 m. The void volumes of the resins in the columns were: 11.5 liters for column 1, 10.9 liters for column 2, 11.3 liters for column 3, 15.8 liters for column 4, and 15.1 liters for column 5. The columns were packed with a strong acid gel type cation exchange resin (manufactured by Rinex) in Mg$^{2+}$ form. The divinylbenzene content of the resin was 65%, and the mean bead size of the resin was 0.38 mm.

Before the separation. Mg$^{2+}$ sulfite spent liquor was pre-coat filtered by using Arbocel B800 as a filter aid. The feed dry substance was then adjusted with a recycle fraction to 49.4 g/100 g and the feed liquor pH was 3.1. The feed was composed as set forth below, whereby the percentages are given on a dry substance weight basis.

TABLE E3-1

| Composition of the feed, % on DS | |
|---|---|
| Glucose | 2.4 |
| Xylose | 17.8 |
| Galactose + rhamnose | 1.9 |
| Arabinose + mannose | 2.2 |
| Lignosulfonates | 45.4 |
| Others (mostly salts) | 30.3 |

The fractionation was performed by way of a 10-step SMB sequence in an equilibrium state, as set forth below, by utilizing a performance mode with three separate loops, namely columns 1 to 3, columns 4 and 5, and all five columns.

Figure 1:
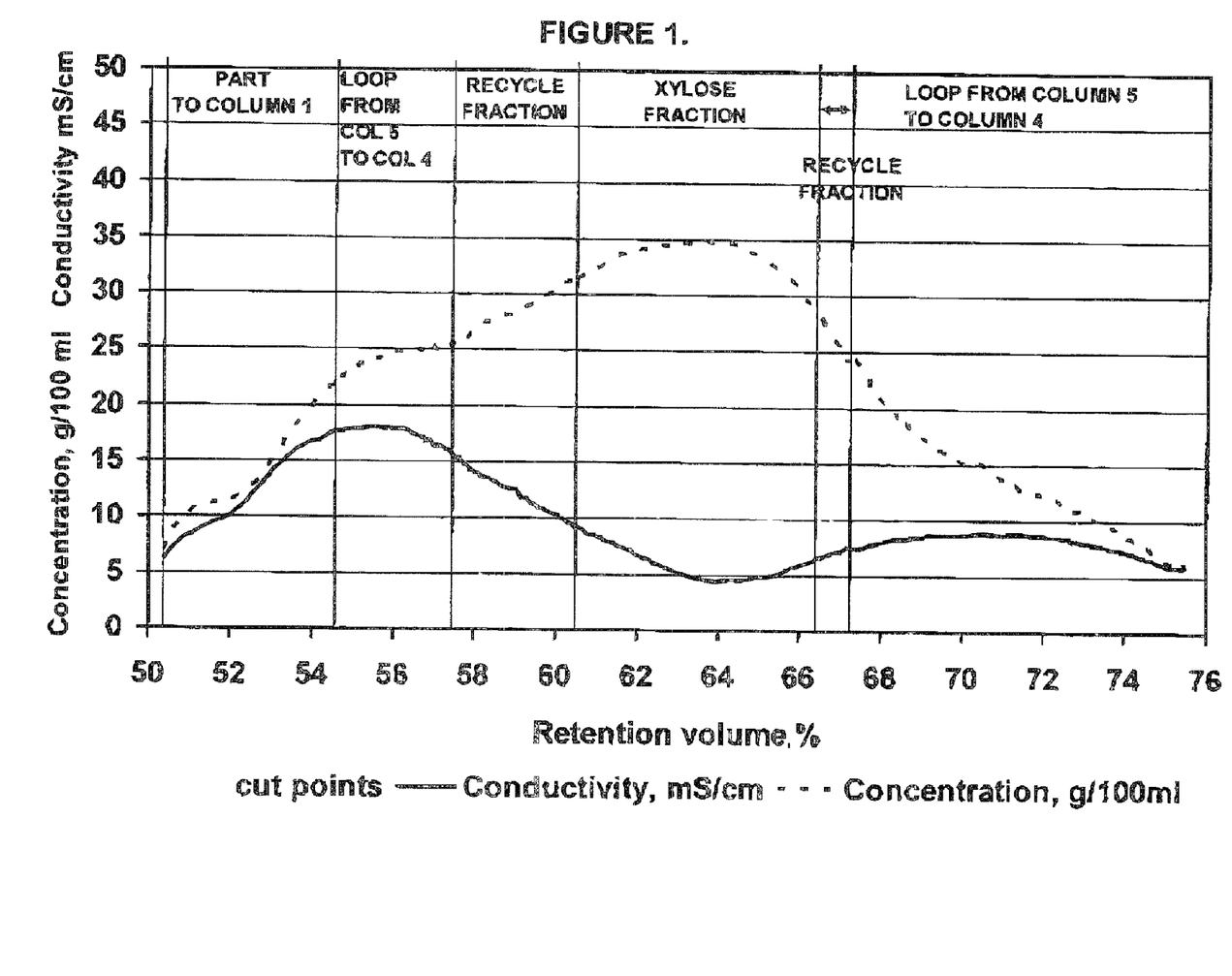
FIG. 1 shows the separation profile from column 5 of the fivecolumn separation system of Example 3 relating to the separation of xylose from $Mg^{2+}$ sulfite spent liquor.

The 10-step sequence (cycle) is shown in FIG. 1, The aim of the separation was to separate xylose contained therein. The feed and the eluent were used at a temperature of 65° C., and 2 weight-% acetic acid solution was used as an eluent.

Step 1: 3.8 l of feed solution was pumped into the first column at a flow rate of 60 l/h and a recycle fraction 1 was collected from the third column. The recycle 1 fraction contains a portion (2.7 liters) of PART 5-2 (=Residual 5 from the cycle one before the previous cycle). A front of PART 5-1 (=Residual 5 profile from a previous cycle) is moved in column 2 replacing 8.1 liters of the void volume of the resin. Simultaneously, 2.0 l was circulated in the column loop, formed with columns 4 and 5, at a flow rate of 33 l/h. A front of PART 5-2/part 2 (1.9 liters) moved from column 5 to the top of the column 4.

Step 2: 8.0 l of feed solution was pumped into the first column at a flow rate of 50 l/h, and a residual fraction 1, containing the fastest-moving components of the feed after Residual 3 (4.9 liters) in step 9, PART 5-2 and also tails of Residual 5 was eventually withdrawn from the same column. Simultaneously, 5.8 l of fresh eluent (water) was pumped into the second column at a flow rate of 37 l/h, and a recycle fraction 2 was collected from column 5. A front of PART 5-1 profile moved 3 liters to column 3.

The front of PART 5-2/part 2 profile (1.9 liters) moved in column 4 to the location 7.7 liters over the void. 0.9 liters of PART 5-2/part 2 profile was withdrawn from the bottom of column 5 to the recycling fraction 1.

Step 3: 4.5 l of feed solution was pumped into the first column in an open loop of all columns at a flow rate of 55 l/h, and a xylose fraction was collected from column 5. A front of PART 5-1 profile moved in column 3 to the location 7.5 liters over the void. The front of PART 5-2/part 2 profile (1.9 liters) moved in column 4 to the location 12.2 liters over the void.

Step 4: 6.4 l of feed solution was pumped into the first column at a flow rate of 51 l/h. Simultaneously, 6.4 liters of the eluent substitute fraction called R-Elu1 including 1.9 liters of the front of PART 5-2/part 2 profile was collected from the fourth column into a separate tank. PART 5-1 is divided to two separate streams. 2.6 liters of the front of PART 5-1/part 2 moved to columns 4. 5 liters of PART 5-1/part 1 remains in the bottom of the column 3. Simultaneously, 8.5 l of fresh eluent was pumped into column 5 at a flow rate of 66 l/h, and 7.0 l of xylose fraction and thereafter 1.5 l of recycle fraction 2 was collected from the same column, Step 5: 2.1 l of feed solution was pumped into the first column at a flow rate of 55 l/h, and a residual fraction 2/1 containing the fastest-moving components of the feed was collected from the second column. Simultaneously, 0.8 l of eluent was pumped into the fifth column at a flow rate of 70 l/h and an eluent replacement fraction R Elu2 was collected from the fourth column. The front of PART 5-1/part 2 profile moved 3.4 liters to column 4. Column 3 was waiting for the next step.

Step 6: First, 0.4 l of fresh eluent (water) and then 7.2 l of the eluent substitute fraction (=R Elu1+R Elu2) collected in Steps 4 and 5 from column 4 into the tank was pumped into the third column at a flow rate of 75 l/h, and a residual fraction 2/2 was collected from the second column. PART 5-1/part 1 at the bottom of column 3 moves to column 1, and the front of Residual 5 (part 1) profile is located at 7.6 liters in column 1. Simultaneously, 15.1 l was circulated in the column loop, formed with columns 4 and 5, at a flow rate of 29.5 l/h. The front of PART 5-1/part 2 profile moved from column 4 to column 5 to the location 2.7 liters over the void.

Step 7: 11.3 l was circulated in the column loop, formed with columns 1 and 2 and 3, at a flow rate of 75 l/h. The front of PART 5-1/part 1 profile is located at 7.4 liters over the void in column 2. Simultaneously, circulation in the column loop, formed with columns 4 and 5, was continued at a flow rate of 29.5 l/h.

Step 8: 1.8 l of fresh eluent (water) was pumped into the first column at a flow rate of 75 l/h and a residual fraction 3/1 containing again the fastest-moving components of the feed was eventually withdrawn from the third column. The front of PART 5-1/part 1 profile is located at 9.2 liters over the void in column 2. Columns 4 and 5 were waiting for the next step, and a new Residual 5 fraction was waiting at the bottom of column 5.

Step 9: In an open loop connecting columns 4, 5, 1, 2 and 3 in that order, 8.1 l of fresh eluent (water) was pumped into the fourth column at a flow rate of 70 l/h, and simultaneously, 8.1 l of a residual fraction (new Residual 5=PART 5) from column 5 was moved to the first column to act as a substitute of eluent as an undisturbed partial profile. The front of PART 5-1/part 1 profile is moved from the column 2 to 6.4 liters over the void in column 3. 8.1 liters of a residual fraction Residual 3/2 is eventually withdrawn from the third column. The front of PART 5-1/part 2 profile (2.6 liters) moved in column 5 to the location 10.7 liters over the void.

Step 10: 7.7 l was circulated in the column loop, formed with columns 1, 2 and 3, at a flow rate of 75 l/h. The front of PART 5 (new Residual 5) profile has moved 4.3 liters over the void in column 2. The front part of PART 5-1/part 1 profile is moved from column 3 to column 1 to the location 2.8 liters over the void. Simultaneously, 3.5 l was circulated in the column loop, formed with columns 4 and 5, at a flow rate of 35 l/h. The front of PART 5-1/part 2 profile (2.6 liters) moved in column 5 to the bottom of the column.

After equilibration of the system, the following fractions were withdrawn from the system: a residual fraction (lignosulfonates, salts) from columns 1, 2 and 3, eluent substitute fractions (R Elu) from column 4 into a tank to be reused, recycle fractions from columns 3 and 5 to be used for the dilution of the feed and xylose product fractions from the last column. In step 9, the eluent substitute fraction (part of lignosulfonates and salts) from column 5 (PART 5) was directly moved as an undisturbed profile to column 1. The results, including HPLC analyses for the combined residual, recycle and xylose fractions, are set forth in the table below.

TABLE E3-2

|  | Combined residual | Combined Recycle | Combined Xylose |
|---|---|---|---|
| Volume, l | 27.6 | 11.1 | 11.5 |
| Dry solids, weight-% | 27.9 | 26.7 | 28.8 |
| Dry solids, g/100 ml | 30.9 | 29.4 | 32.0 |
| Glucose, % on DS | 0.6 | 4.7 | 4.4 |
| Xylose, % on DS | 0.4 | 22.8 | 52.2 |
| Galactose + rhamnose, % on DS | 0.2 | 2.8 | 5.2 |
| Arabinose + mannose, % on DS | 0.2 | 3.1 | 5.8 |
| Others, % on DS | 98.6 | 66.6 | 32.4 |

The overall xylose yield calculated from these fractions was 98.4%. In the test run, 8.1 l of column 5 Residual 5 (PART 5) was introduced into column 1 as an eluent substitute in step 9. Also 7.2 l of column 4 Residual 4 was is collected into a tank as an eluent substitute fraction in steps 4 and 5, and fed to column 3 as an eluent substitute in step 6. The W/F (water to feed) ratio was only 1.0. The saving in the fresh eluent water was 39% as compared with the same mode without eluent substitutions in step 9 and in steps 4 to 6.

The dry substance components of the PART 5 (=Residual 5) that was used to replace the eluent in step 9 raised the dry substance contents of all residual fractions (1, 2/1, 2/2, 3/1, and 3/2) and recycle fractions 1 and 2. During the next cycle, a portion of the PART went to Residual 1. Some of the PART went to loop 2 during step 4, where it stayed during the first cycle, Also in loop 1, a portion of the PART stayed in the loop during the first cycle.

During the next cycle, the rest of the dry substance in loop 1 was collected in Residual 1 in step 2 and a recycle fraction is collected in step 1. In loop 2, the PART was collected to Residual 4 in step 4.

The external recycling of the eluent substitute solution (the part called R Elu) in step 6 had some of the dry substance recycled internally in step 9. During the first cycle, most of the PART went into Residual 3 in steps 8 and 9. The rest of the PART stayed in the first loop until the next cycle.

During the next cycle, a portion of the recycled dry substance was collected into a recycle fraction in step 1. The rest went to loop 2 until the part was recycled back to loop 1 in step 9. The rest of the dry substance stayed in the second loop until the next round.

During the third cycle, the rest of the externally recycled dry substance was collected into an eluent substitute fraction (R Elu) in steps 4 and 5.

In the equilibrium state, this new way to use the steps creates an internal loop for the components of the PART, raising the dry substance content of the residual fractions without affecting the xylose yield or the purity of the xylose fraction.

A simplified calculation of the movement of the PART and its components was done assuming that the void volume is 33% of the bed volume and lignosulfonates and salts have no retention on the resin. Also a band broadening was taken into account to some extent, counting that a volume expansion of PART is approximately 50%. The profile front movement of the residual fraction was calculated by subtracting the volume of a step from the column void, starting with the step where the eluent was replaced by the eluent substitute solution (R Elu). This method is very accurate for the profile front movement. Tailing of the profile was an estimate, and it was shown by this example that some tailing is evident but it did not deteriorate the xylose fraction.

The eluent substitute fed in step 9 goes in front of the profile as a prefeed, and during the next cycle in step 7, the recycled dry substance is fed to column 1 behind the profile as post feed.

EXAMPLE 4

Chromatographic Separation of CaSSL-batch Separation

The test equipment included a separation column, a feed pump, a heat exchanger, inlet valves for the feed and the eluent as well as flow control means for out-coming liquid. The equipment also included a tank, a feed pump, lines, flow control means and valves for the PART fraction and for the front feed. The height of the chromatographic resin bed in the separation was 8.0 m, and the column consisted of four compartments (2.1 m/2.1 m/1.8 m/2.0 m), All columns had a diameter of 0.111 m. The column was packed with a strong acid gel type cation exchange resin (manufactured by Finex) in $Ca^{2+}$ form. The divinylbenzene content of the resin was 5.5%. The mean bead size of the resin was 0.40 mm.

As a feed, spent liquor from $Ca^{2+}$ based sulfite cooking (CaSSL) was used and the aim was to separate the xylose contained therein.

Before the test, the feed liquor was filtered with a Seitz plate and a frame pressure filter by using Arbocel B800 as a filtering aid (precoat 1 kg/m$^2$, bodyfeed 0.5% on DS basis), and the feed dry substance content was adjusted to 32.1 g/100 g with a separation recycle fraction. The properties of the feed are set forth in the table below, whereby the percentages are given on a dry substance weight basis.

TABLE E4-1

| Composition of CaSSL, % on DS | |
|---|---|
| pH (as is) | 3.1 |
| Xylose | 23.9 |
| Glucose | 1.1 |
| Other sugars | 3.5 |
| Others | 71.5 |

The fractionation was performed by way of a 9-step batch separation sequence as set forth below. The aim of the separation was to separate xylose contained therein. The feed, the eluent water, the front feed and PART were all used at a temperature of 65° C.

Step 1: 10.3 l of feed solution was pumped to the top of the column at a flow rate of 18 l/h, and a residual fraction was collected from the bottom of the column.

Step 2: First, 3.0 l of PART fraction followed by 0.4 l of water was pumped to the top of the column at a flow rate of 18 l/h, and a residual fraction was collected from the bottom of the column.

Step 3: 1.4 l of water was pumped to the top of the column at a flow rate of 18 l/h, and a recycle fraction was collected from the bottom of the column.

Step 4: 2.6 l of water was pumped to the top of the column at a flow rate of 18 l/h, and a front feed fraction was collected from the bottom of the column.

Step 5: 8.0 l of water was pumped to the top of the column at a flow rate of 18 l/h, and a xylose fraction was collected from the bottom of the column.

Step 6: 3.1 l of water was pumped to the top of the column at a flow rate of 18 l/h, and a recycle fraction was collected from the bottom of the column, Step 7: 2.0 l of water was pumped to the top of the column at a flow rate of 18 l/h, and a PART fraction was collected from the bottom of the column.

Step 8: 1.0 l of front feed fraction was pumped to the top of the column at a flow rate of 18 l/h, and a PART fraction was collected from the bottom of the column.

Step 9: 1.6 l of front feed fraction was pumped to the top of the column at a flow rate of 18 l/h, and a residual fraction was collected from the bottom of the column.

After equilibration of the system with several feeds, the following fractions were drawn from the separation column product valves: a residual fraction, two recycle fractions (both sides of the xylose peak), a front feed fraction, a xylose product fraction and PART fraction. The results, including HPLC analyses for the combined fractions, are set forth in the table below.

TABLE E4-2

| | Residual | Recycle | Xylose | Front feed | PART |
|---|---|---|---|---|---|
| Volume, l | 15.3 | 4.5 | 8.0 | 2.6 | 3.0 |
| Dry solids, g/100 ml | 14.3 | 8.8 | 14.7 | 12.4 | 8.2 |
| Xylose, % on DS | 1.6 | 31.7 | 62.9 | 47.9 | 4.1 |
| Glucose, % on DS | 0.5 | 1.5 | 2.0 | 3.8 | 0.0 |
| Other sugars % on DS | 0.5 | 7.6 | 7.8 | 3.9 | 5.7 |
| Others, % on DS | 97.4 | 59.2 | 27.3 | 44.4 | 90.2 |

The yield calculated from the product fractions was 95.5% for xylose. In the separation, a portion of the residual fraction (3.0 l) was collected as a PART fraction and used as an eluent replacement. The PART fraction was introduced right after the feed, which allowed fast components (like lignosulfonates, salts) present in the PART fraction to pass the xylose fraction and slow components (like xylonic acid, arabinose) to be retarded even more during the separation. The use of the PART fraction reduced the use of fresh eluent by 14.6% without any effect on the product fraction yield or purity. The W/F ratio for the separation was 1.7.

EXAMPLE 5

Dilute Glucose Fraction Used as an Eluent in Glucose-fructose SMB Separation

The process equipment included three columns connected in series, a feed pump, recycling pumps, an eluent water pump, heat exchangers, flow control means for out-coming liquids as well as inlet and product valves for the various process streams. The equipment also included a tank, dilute glucose feed pump, lines, flow control means and valves for dilute glucose to be used as an eluent water replacement. The height of each column was 4.0 m, and each column had a diameter of 0.2 m and a resin volume of 125 liters each. The columns were packed with a strong acid gel type cation exchange resin (manufactured by Finex) in $Ca^{2+}$-form. The divinylbenzene content of the resin was 5.5%, and the mean bead size of the resin was 0.36 mm.

As a feed, inverted sucrose was used, and the aim was to separate glucose and fructose into different fractions. The liquor concentration was 64.9 g/100 ml. The feed was composed as set forth below, whereby the percentages are given on a dry substance weight basis.

TABLE E5-1

| Composition of the feed, % on DS | |
|---|---|
| Fructose | 49.2 |
| Glucose | 49.0 |
| Disaccharides | 0.8 |
| Others | 1.0 |

The fractionation was performed by way of a 15-step SMB sequence as set forth below. The feed and the eluent were used at a temperature of 65° C. Water was used as an eluent. A dilute portion of glucose fraction from all columns was collected into a tank to be used as an eluent replacement (PART).

Step 1: 8.2 l of water was pumped into the second column at a flow rate of 130 l/h, and a dilute glucose fraction was collected from the first column Step 2: 17.9 l of feed solution was pumped into the first column at a flow rate of 110 l/h, and a glucose fraction was collected from the same column. Simultaneously, 18.4 l of water was pumped into the second column at a flow rate of 110 l/h, and a fructose fraction was collected from the same column. Column 3 was waiting for the next step.

Step 3: 1.8 l of water was pumped into the second column at a flow rate of 120 l/h, and a glucose fraction was collected from the first column.

Step 4: 8.2 l of dilute glucose fraction was pumped into the second column at a flow rate of 120 l/h, and a glucose fraction was collected from the first column.

Step 5: 58.8 l was circulated in the column set loop, formed with all columns, at a flow rate of 130 l/h.

Step 6: 8.2 l of water was pumped into the third column at a flow rate of 130 l/h, and a dilute glucose fraction was collected from the second column.

Step 7: 17.9 l of feed solution was pumped into the second column at a flow rate of 110 l/h, and a glucose fraction was collected from the same column. Simultaneously, 18.4 l of water was pumped into the third column at a flow rate of 110 l/h, and a fructose fraction was collected from the same column. Column 1 was waiting for the next step.

Step 8: 1.8 l of water was pumped into the third column at a flow rate of 120 l/h, and a glucose fraction was collected from the second column.

Step 9: 8.2 l of dilute glucose fraction was pumped into the third column at a flow rate of 120 l/h, and a glucose fraction was collected from the second column.

Step 10: 58.8 l was circulated in the column set loop, formed with all columns, at a flow rate of 130 l/h.

Step 11: 8.2 l of water was pumped into the first column at a flow rate of 130 l/h, and a dilute glucose fraction was collected from the third column.

Step 12: 179 l of feed solution was pumped into the third column at a flow rate of 110 l/h, and a glucose fraction was collected from the same column. Simultaneously, 18.4 l of water was pumped into the first column at a flow rate of 110 l/h, and a fructose fraction was collected from the same column, Column 2 was waiting for the next step.

Step 13: 1.8 l of water was pumped into the first column at a flow rate of 120 l/h, and a glucose fraction was collected from the third column.

Step 14: 8.2 l of dilute glucose fraction was pumped into the first column at a flow rate of 120 l/h, and a glucose fraction was collected from the third column.

Step 16: 58.8 l was circulated in the column set loop, formed with all columns, at a flow rate of 130 l/h After equilibration of the system, the following fractions were drawn from the system: One dilute glucose-enriched fraction (PART) from each column, one glucose-enriched fraction from each column, and one fructose-enriched fraction from each column. Dilute glucose fractions (PART's) from each column were used as an eluent water replacement. The results including HPLC analyses for the combined fractions are set forth in the table below.

TABLE E5-2

| | Combined fructose | Combined glucose | Dilute glucose |
|---|---|---|---|
| Volume, l | 55.2 | 83.7 | 24.6 |
| Dry solids, g/100 ml | 30.6 | 21.1 | 2.8 |
| Fructose, % on DS | 96.2 | 2.9 | 0.5 |
| Glucose, % on DS | 0.6 | 94.3 | 92.4 |
| Disaccharides, % on DS | 0.5 | 1.4 | 5.0 |
| Others, % on DS | 2.7 | 1.4 | 2.1 |

The overall fructose yield calculated from these fractions was 96.9%. The W/F ratio for the separation was 1.6 and over 20% of glucose fraction was re-used as an eluent substitute to reduce the evaporation demand.

EXAMPLE 6

Fructose Crystallization Run-off Separation

The process equipment includes two columns connected in series, a feed pump, recycling pumps, an eluent water pump, heat exchangers, flow control means for out-coming liquids as well as inlet and product valves for the various process streams. The equipment also includes a tank, a PART feed pump, lines, flow control means and valves for the PART fraction to be used as an eluent water replacement. The height of both columns is 3.95 m, and both columns have a diameter of 0.2 m. The columns are packed with a strong acid gel type cation exchange resin (manufactured by Finex) in $Na^+$ form. The divinylbenzene content of the resin is 5.5% and the mean bead size of the resin is 0.36 mm.

As a feed, a fructose crystallization run-off is used, and the aim is to separate the fructose contained therein.

The liquor concentration is 66.1 g/100 ml, and the pH is 3.8. The fructose crystallization run-off is composed as set forth below, whereby the percentages are given on a dry substance weight basis.

TABLE E6-1

| Composition of the feed, % on DS | |
|---|---|
| Fructose | 92.0 |
| Glucose | 2.7 |
| Disaccharides A | 1.9 |
| Disaccharides B | 1.7 |
| Others | 1.7 |

The fractionation is performed according to U.S. Pat. No. 6,896,811 circulating the separation profile 1.5 times through the separation bed by way of a 14-step SMB sequence as set forth below. The feed and the eluent are used at a temperature of 65° C. and water is used as an eluent.

Step 1: 13 l of feed solution is pumped into the first column at a flow rate of 90 l/h, and a recycle fraction is collected from the second column. During the end of this step, approximately 4 l of separation profile to be used as a PART fraction is transferred to the second column.

Step 2: 22 l of feed solution is pumped into the first column at a flow rate of 90 l/h, and a residual fraction is collected from the same column. Simultaneously, 8 l of PART fraction followed by 39 l of water are pumped into the second column at a flow rate of 190 l/h, and fructose fraction is collected from the same column.

Step 3: 54 l is circulated in the column set loop, formed with all columns, at a flow rate of 90 l/h.

Step 4: 24 l of water is pumped into the first column at a flow rate of 90 l/h, and first, 4 l of PART fraction, followed by 20 l of residual fraction are collected from the second column.

Step 5: 57 l is circulated in the column set loop, formed with all columns, at a flow rate of 90 l/h.

Step 6: 25 l of water is pumped into the second column at a flow rate of 90 l/h, and first, 4 l of PART fraction, followed by 21 l of a residual fraction, are collected from the first column.

Step 7: 48 l is circulated in the column set loop, formed with all columns, at a flow rate of 90 l/h.

Step 8: 13 l of feed solution is pumped into the second column at a flow rate of 90 l/h, and a recycle fraction is collected from the first column. During the end of this step, approximately 4 l of separation profile to be used as a PART fraction is transferred to the first column.

Step 9: 22 l of feed solution is pumped into the second column at a flow rate of 90 l/h, and a residual fraction is collected from the same column. Simultaneously, 8 l of PART fraction followed by 39 l of water, are pumped into the first column at a flow rate of 190 l/h, and fructose fraction is collected from the same column.

Step 10: 54 l is circulated in the column set loop, formed with all columns, at a flow rate of 90 l/h.

Step 11: 24 l of water is pumped into the second column at a flow rate of 90 l/h, and first, 4 l of PART fraction, followed by 20 l of residual fraction, are collected from the first column.

Step 12: 57 l is circulated in the column set loop, formed with all columns, at a flow rate of 90 l/h.

Step 13: 25 l of water is pumped into the first column at a flow rate of 90 l/h, and first, 4 l of PART fraction, followed by 21 l of residual fraction, are collected from the second column.

Step 14: 48 l are circulated in the column set loop, formed with all columns, at a flow rate of 90 l/h.

After equilibration of the system, the following fractions are drawn from the system. Two PART fractions from both columns, three residual fractions from both columns, one fructose-containing fraction and one recycle fraction from both columns. The results, including HPLC analyses for the combined fractions, are set forth in the table below,

TABLE E6-2

|  | Fructose | Residual | Recycle | PART |
|---|---|---|---|---|
| Volume, l | 94.0 | 126.0 | 26.0 | 16.0 |
| Dry solids, g/100 ml | 38.8 | 2.0 | 28.2 | 0.85 |
| Fructose, % on DS | 94.9 | 55.4 | 91.3 | 41.2 |
| Glucose, % on DS | 1.3 | 19.6 | 3.9 | 21.5 |
| Disaccharides A, % on DS | 0.6 | 8.7 | 1.5 | 8.2 |
| Disaccharides B, % on DS | 0.7 | 8.7 | 1.3 | 13.1 |
| Others, % on DS | 2.5 | 7.6 | 2.0 | 16.0 |

The overall fructose yield calculated from these fractions is 96.1%. The W/M ratio for the separation is 2.5. Over 15% of the residual fraction is used as a PART fraction to substitute the eluent and reduce the evaporation demand,

EXAMPLE 7

Maltose Hydrolysate Separation

The process equipment includes two columns connected in series, a feed pump, recycling pumps, an eluent water pump, heat exchangers, flow control means for out-coming liquids as well as inlet and product valves for the various process streams. The equipment also includes a tank, a PART feed pump, lines, flow control means and valves for the PART fraction to be used as an eluent water replacement. The height of both columns is 4.04 m, and both columns have a diameter of 0.2 m. The columns are packed with a strong acid gel type cation exchange resin (manufactured by Finex) in $Na^+$ form. The divinylbenzene content of the resin is 5.5%, and the mean bead size of the resin is 0.33 mm.

As a feed, maltose hydrolysate is used, and the aim is to separate the maltose contained therein.

The liquor concentration is 56.4 g/100 ml and the pH is 4.4. The maltose hydrolysate is composed as set forth below, whereby the percentages are given on a dry substance weight basis.

TABLE E7-1

| Composition of the feed, % on DS | |
|---|---|
| Oligomers | 2.6 |
| Maltotriose | 1.4 |
| Glucose | 6.5 |
| Maltose | 85.3 |
| Others | 4.2 |

The fractionation is performed by way of a 10-step SMB sequence as set forth below. The feed and the eluent are used at a temperature of 60° C., and water is used as an eluent.

Step 1: 14 l of feed solution is pumped into the first column at a flow rate of 63 l/h, and a recycle fraction is collected from the second column.

Step 2: 18 l of feed solution is pumped into the first column at a flow rate of 42 l/h, and a residual fraction is collected from the same column. Simultaneously, first, 12 l of water, followed by 12 l of PART fraction, and finally 21 l of water are pumped into the second column at a flow rate of 110 l/h, and a maltose fraction is collected from the same column.

Step 3: 8 l of feed solution is pumped into the first column at a flow rate of 63 l/h, and a maltose fraction is collected from the second column.

Step 4: 35.9 l is circulated in the column set loop, formed with all columns, at a flow rate of 63 l/h.

Step 5: 17 l of water is pumped into the first column at a flow rate of 63 l/h, and first, 4 l of PART fraction, followed by 13 l of residual fraction, are collected from the second column.

Step 6: 41.9 l is circulated in the column set loop, formed with all columns, at a flow rate of 63 l/h.

Step 7: 21 l of water is pumped into the second column at a flow rate of 63 l/h, and first, 4 l of PART fraction, followed by 17 l of residual fraction, are collected from the first column.

Step 8: 41.9 l is circulated in the column set loop, formed with all columns, at a flow rate of 63 l/h.

Step 9: 21 l of water is pumped into the first column at a flow rate of 63 l/h, and first, 4 l of PART fraction, followed by 17 l of residual fraction, are collected from the second column.

Step 10: 31.9 l is circulated in the column set loop, formed with all columns, at a flow rate of 63 l/h.

After equilibration of the system, the following fractions are drawn from the system. Three PART fractions, four residual fractions, two maltose-containing fractions and one recycle fraction. The results, including HPLC analyses for the combined fractions, are set forth in the table below.

TABLE E7-2

|  | Maltose | Residual | Recycle | PART |
|---|---|---|---|---|
| Volume, l | 53.0 | 65.0 | 14.0 | 12.0 |
| Dry solids, g/100 ml | 31.2 | 5.0 | 18.0 | 5.1 |
| Oligomers, % on DS | 0.3 | 15.4 | 2.3 | 12.2 |
| Maltotriose, % on DS | 0.8 | 4.4 | 3.2 | 3.1 |
| Glucose, % on DS | 1.5 | 34.2 | 5.8 | 44.2 |
| Maltose, % on DS | 96.9 | 26.0 | 87.7 | 9.7 |
| Others, % on DS | 0.5 | 20.0 | 1.0 | 30.8 |

The overall maltose yield calculated from these fractions is 95.0%. The W/F ratio for the separation is 2.3. Over 15% of the residual fraction is used as a PART fraction to substitute the eluent and reduce the evaporation demand.

EXAMPLE 8

Chromatographic SMB Separation of Vinasse

The process equipment included six columns connected in series, a feed pump, circulation pumps, an eluent water pump, heat exchangers, flow control means for out-coming liquids as well as inlet and product valves for the various process streams. The height of first four columns was 2 m, and the height of last two columns was 1.5 m, and each column had a diameter of 0.2 m (except the first one 0.21 m). The first four columns (having a total volume of 254 l) were packed with a strong acid gel type cation exchange resin (manufactured by Mitsubishi) in $Na^+$ form. The divinylbenzene content of the resin was 6.0%, and the mean bead size of the resin was 0.2 mm. The last two columns 5 and 6 (having a total volume of 95 l, which comprises 27% of the total volume of the separation system) were packed with a weakly acidic gel type cation exchange resin (manufactured by Finex) in $H^+$ form. The divinylbenzene content of the resin was 8.0%, and the mean bead size of the resin was 0.43 mm.

Before the separation, vinasse liquor was diluted with water to ca. 45 weight-% and microfiltrated by using Scepter 0.1 μm membrane. The pH was adjusted to a range of 5.5 to 6.0 with NaOH, and after this, vinasse was pre-coat filtered using diatomaceous earth as a filter aid. The amount of the pre-coat was 1 kg/m², the amount of the body feed was 0.5% on DS, and the temperature was 80° C. The feed was composed as set forth below, whereby the percentages are given on a DS basis.

TABLE E8-1

| Composition of the feed, % on DS | |
|---|---|
| Feed DS g/100 g | 37.8 |
| Betaine | 15.9 |
| Glycerol | 12.5 |
| Inositol | 0.5 |
| Fructose | 1.7 |
| Others | 69.4 |
| pH | 5.13 |

The fractionation was performed by way of a 10-step SMB sequence as set forth below. The aim of the separation was to separate betaine and to recycle glycerol back into the SAC separation in order to reduce eluent water consumption as well as to get most of the glycerol to be eluted out in residual fractions. The feed and the eluent were used at a temperature of 80° C., and ion exchanged water was used as the eluent.

Step 1: 7.0 l of feed solution was pumped into the first column at a flow rate of 65 and a recycle fraction was collected from the fourth column. Simultaneously, 4.0 l was circulated in the column loop, formed with columns five and six, at a flow rate of 40 l/h.

Step 2: 10.0 l of feed solution was pumped into the first column at a flow rate of 65 l/h, and a recycle fraction was collected from the sixth column. Simultaneously, a portion of a part of the separation profile enriched in betaine and glycerol was transferred from the SAC bed (from column 4) to the WAC bed (to column 5).

Step 3: 9.0 of feed solution was pumped into the first column at a flow rate of 65 l/h, and a residual fraction was collected from the third column. Simultaneously, 8.0 l of water was pumped into the fourth column at a flow rate of 40 l/h, and a betaine fraction was collected from the last column. Simultaneously, a portion of a part of the separation profile enriched in betaine and glycerol was transferred from the SAC bed (from column 4) to the WAC bed (to column 5).

Step 4: The first column was on hold during this step. 8.0 l of feed solution was pumped into the second column at a flow rate of 65 l/h, and a residual fraction was collected from the third column. Simultaneously, 4.0 l of water was pumped into the fourth column at a flow rate of 65 l/h, and a betaine fraction was collected from last column Simultaneously, a portion of a part of the separation profile enriched in betaine and glycerol was transferred from the SAC bed (from column 4) to the WAC bed (to column 5).

Step 5: 4.0 l of feed solution was pumped into the first column at a flow rate of 40 l/h, and a residual fraction was collected from the same column. Simultaneously, 13.0 l of water was pumped into second column, and a betaine fraction was collected from the last column. Simultaneously, a portion of a part of the separation profile enriched in betaine and glycerol was transferred from the SAC bed (from column 4) to the WAC bed (to column 5).

Step 6: 6.0 l of water was pumped into the second column having a circulation loop from the fourth column into the first column at a flow rate of 65 l/h, and a residual fraction was collected from the first column. Simultaneously, 5.0 l circulation was started in the column loop, formed with columns 5 and 6, at a flow rate of 55 l/h.

Step 7: 11.0 l circulation in the column loop, formed with columns 1, 2, 3 and 4, at a flow rate of 65 l/h, and simultaneously, 6.0 l circulation was continued in the column loop, formed with columns 5 and 6, at a flow rate of 35 l/h.

Step 8: 6.0 l of water was pumped into the fifth column at a flow rate of 65 l/h, and a glycerol circulation fraction was circulated from column 6 to column 1, and a residual fraction was collected from the fourth column.

Step 9: 20.0 l of water was pumped into the fifth column at a flow rate of 65 l/h, and a glycerol circulation fraction was circulated from column 6 to column 1, and a residual fraction was collected from the second column. Simultaneously, 20.0 l of water was pumped into the third column, and a residual fraction was collected from the fourth column at a flow rate of 65 l/h.

Step 10: 10.0 l of water was pumped into the fifth column at a flow rate of 65 l/h, and a glycerol circulation fraction from column 6 was circulated to column 3, and outflow from column 4 was circulated into column 1, and a residual fraction was collected from the second column.

The volume of the WAC bed was 27% of the total resin bed volume of the separation system. The volume of the transfer fraction (a part of the separation profile enriched in betaine and glycerol) transferred from column 4 to column 5 (from the SAC bed to the WAC bed) in steps 2, 3, 4 and 5 was 35 l (37% of the volume of the WAC bed).

After equilibration of the system, the following fractions were drawn from the system: a residual fraction from columns 1, 2, 3 and 4, recycle fractions from the fourth column and betaine product fraction from the last column. The results, including HPLC analyses for the combined fractions, are set forth in the table below.

TABLE E8-2

|  | Combined residual | Recycle | Betaine |
|---|---|---|---|
| Volume, l | 83.0 | 17.0 | 25.0 |
| Dry solids, g/100 ml | 12.9 | 8.4 | 5.3 |
| Betaine, % on DS | 2.6 | 41.4 | 85.0 |
| Glycerol, % on DS | 8.9 | 38.0 | 6.4 |
| Inositol, % on DS | 0.5 | 1.2 | 0.2 |
| Fructose, % on DS | 1.3 | 5.5 | 0.3 |
| Others, % on DS | 86.7 | 14.0 | 8.3 |

The overall betaine yield calculated from these fractions was 80.0%. Glycerol fraction from the WAC resin bed was introduced into columns between succesive feeds (steps 8 and 9) or profiles (step 10) to be withdrawn in residual fractions together with salts. In this example, a glycerol circulation fraction was circulated back to columns 1 and 3. Over 95% of the glycerol of the feed was withdrawn from columns filled with the SAC resin. Thereof, about 60% of glycerol was withdrawn in residual fractions and 35% of glycerol was withdrawn in a recycle fraction. The dry solids content of the residual fractions was increased, and the volume of the residual fractions was reduced by circulating a part of the residual fractions from columns 1 and 3 in order to get them to elute simultaneously with residual fractions of the following profile(s). Only residual and betaine fractions were taken out from the system, and the W/F (water to feed) ratio was 3.2. When the residual and betaine fractions are evaporated to 60 weight-%, the condensate removal is 81.4 kg per kg betaine. The evaporation demand was reduced 21% as compared with a test run, where glycerol was not introduced back to the separation.

EXAMPLE 9

Chromatographic SMB Separation of Beet Molasses—Betaine-containing Parts

The process equipment included three columns connected in series, a feed pump, recycling pumps, an eluent water pump, heat exchangers, flow control means for out-coming liquids as well as inlet and product valves for the various process streams. The equipment also included an eluent replacement tank, a feed pump for the eluent replacement solution, lines, flow control means and valves for the fractions to be used as an eluent water replacement. The height of all three columns was 5.0 m, and their diameter was 0.111 m. The total resin bed volume of the three-column system was 3×48.4 l=145.2 liters. The columns were packed with a strong acid gel type cation exchange resin (manufactured by Finex) in $Na^+$ form. The divinylbenzene content of the resin was 5.5%, and the mean bead size of the resin was 0.33 mm.

Before the separation, beet molasses was diluted with ion exchanged water to 60 weight-% and 1.5% sodium carbonate on DS was added. The solution was then pH-adjusted with NaOH to a pH of about 9.7, heated to 60° C., and cooled down to 40° C. during 15 hours of mixing. After this, beet molasses was pre-coat filtered using diatomaceous earth as a filter aid. The amount of the pre-coat was 1 $kg/m^2$, the amount of the body feed was 0.5% on DS, and the temperature was 60° C. A final pH adjustment was carried out with HCl to pH 8.6.

For the separation tests, the beet molasses was still evaporated to 78 weight-% and filtered through 5 μm bag filter. During the tests, the feed dry substance was adjusted by mixing 78 weight-% beet molasses with a collected recycle fraction in a separate tank before feeding it to the column. The feed in the test was composed as set forth below, whereby the percentages are given on a dry substance weight basis.

TABLE E9-1

| Composition of feed | |
|---|---|
| Dry solids, weight-% | 45.6 |
| Sucrose, % on DS | 60.3 |
| Betaine, % on DS | 4.0 |
| Others, % on DS | 35.7 |

The fractionation was performed by way of A sequential simulated moving bed (SMB) system by using a special process mode described in U.S. Pat. No. 6,896,811 by circulating the formed separation profile twice through the resin bed of the SMB system and using of a 16-step SMB sequence as set forth below. The aim of the separation was to separate sucrose and betaine contained therein. The feed and the eluent were used at a temperature of 80° C., and ion exchanged water was used as an eluent.

Step 1: 2.8 l of feed solution was pumped into the first column at a flow rate of 50 l/h, and a sucrose recycle fraction was collected from the last column.

Step 2: 10.4 l of feed solution was pumped into the first column at a flow rate of 33 l/h, and first, 4.0 l of betaine containing PART (B1+R1) and then 6.4 l of a residual fraction was collected from the same column. Simultaneously, 19.4 l of eluent was pumped into the second column at a flow rate of 79 l/h, and first, 8.7 l of a recycle fraction and then 10.7 l of sucrose recycle fraction was collected from the last column.

Step 3: 6.0 l of feed solution was pumped into the first column at a flow rate of 55 l/h, and a sucrose fraction was collected from the last column.

Step 4: 7.6 l was circulated in the column loop, formed with all columns, at a flow rate of 60 l/h.

Step 5: 4.5 l of eluent was pumped into the third column at a flow rate of 60 l/h, and a residual fraction was collected from the second column.

Step 6: 14.8 l of eluent was pumped into the third column at a flow rate of 70 l/h, and first, 2.0 l of betaine containing PART (B2), then 10.8 l of betaine fraction, and finally 2.0 l of betaine containing PART (B3) were collected from the last column. PART fractions were collected into a separate tank and used as an eluent replacement.

Step 7: 17.3 l was circulated in the column loop, formed with all columns, at a flow rate of 65 l/h. The circulation was continued 4 liters more than in the reference test to use a part of the residual fraction from column 3 as a PART (R 3) in dilute concentration as a replacer of the water eluent. The movement of the front of the PART (R 3) components (salts, organic acids etc.) is calculated by using a retention volume of 30% BV.

Step 8: 7.5 l of eluent water was pumped into the first column at a flow rate of 65 l/h, and a residual fraction was collected from the third column.

Step 9: 11.0 l of PART containing betaine and residual components (B1+R1, B2, B3, B4+R3) was pumped into the first column as an eluent water replacement at a flow rate of 60 l/h, and the collection of a residual fraction from the third column was continued. The calculation of the movement of the components in PARTS was done in a manner similar to that used in the previous examples.

Step 10: 16.8 l was circulated in the column loop, formed with all columns, at a flow rate of 70 l/h.

Step 11: 4.1 l of eluent water was pumped into the second column at a flow rate of 65 l/h, and a residual fraction was collected from the first column Step 12: 13.3 l was circulated in the column loop, formed with all columns, at a flow rate of 60 l/h.

Step 13: 15.0 l of eluent water was pumped into the third column at a flow rate of 60 l/h, and a residual fraction was collected from the second column.

Step 14: 13.2 l was circulated in the column loop, formed with all columns, at a flow rate of 70 l/h.

Step 15: 15.0 l of eluent water was pumped into the first column at a flow rate of 65 l/h, and first, 3.0 l of a betaine-containing PART (B4+R3) and than 12.0 l of a residual fraction were collected from the third column. PART (B4+R3) fraction was collected into the separate tank and used as eluent replacement in step 9.

Step 16: 10.7 l was circulated in the column loop, formed with all columns, at a flow rate of 65 l/h.

After equilibration of the system, the following fractions were drawn from the system: two residual fractions from all columns, betaine-containing PART fractions used as an eluent replacement from the first and last columns, recycle fractions from the last column, sucrose product fractions from the last column, and a betaine product fraction from the last column.

The results, including HPLC analyses for the combined residual, recycle, sucrose, betaine and PART fractions, are set forth in the table below.

TABLE E9-2

|  | Combined residual | Combined recycle | Combined sucrose | Combined Betaine | Combined PART |
|---|---|---|---|---|---|
| Volume, l | 60.5 | 11.5 | 16.7 | 10.8 | 11.0 |
| Dry solids, weight-% | 4.7 | 17.2 | 29.1 | 3.4 | 1.8 |
| Dry solids, g/100 ml | 4.8 | 18.3 | 32.6 | 3.4 | 1.8 |
| Sucrose % on DS | 5.5 | 55.5 | 94.6 | 1.0 | 2.3 |
| Betaine, % on DS | 1.2 | 3.3 | 0.1 | 82.0 | 49.7 |
| Others, % on DS | 93.3 | 41.2 | 5.3 | 17.0 | 48.0 |

The overall yield calculated from these fractions is 96.9% for sucrose and 88.4% for betaine. The W/F ratio (vol/vol) for the separation was 4.2. In the experiment, the dry solids content and betaine content of the betaine fraction were increased by circulating betaine from the betaine-containing PART fractions (as four different PARTS) to the recycle fraction and back to the feed solution. In the experiment, the concentration of the residual fraction was increased by circulating residual components from the PART fractions to the residual fractions. The residual fraction was further concentrated by circulating the first part of the residual components inside the separation system in steps 7 and 10. In a reference separation process without taking and recycling PART fractions containing betaine and residual, the betaine yield in the betaine fraction was only 73.1% and the betaine content was 79.5% on DS, the combined residual volume was 73.7 liters and the separation W/F ratio was 4.9.

By using circulations of PARTS, the amount of eluent water was reduced by 18% as compared with the reference run without using the PARTS.

On an industrial scale, the separate intermediate tank for PARTS may serve several SMB systems operating with the same feed molasses. It is also possible to use PART fractions collected from different separations as long as the components present in the PART fractions can be withdrawn in desired product or residual fractions. For example betaine-containing residual fractions from other betaine molasses separations may be used here as a PART fraction.

It will be obvious to a person skilled in the art that, as technology advances, the inventive concept can be implemented in various ways. The invention and its embodiments are not limited to the examples described above but may vary within the scope of the claims.

The invention claimed is:

1. A process for fractionating a solution containing at least one component selected from sugars, sugar alcohols, sugar acids and betaine in a chromatographic separation system, which comprises one or more columns containing one or more partial packed beds, comprising
   feeding the solution into the separation system,
   introducing an eluent into the separation system to elute components of the solution to form a separation profile, and
   recovering one or more product fractions enriched in a product component selected from sugars, sugar alcohols, sugar acids, and betaine, one or more residual fractions, and optionally one or more recycle fractions,
   and further comprising
   introducing one or more parts of the separation profile to one or more eluent introduction positions of the separation system in one or more part feeding phases to substitute a portion of the eluent, said parts comprising one or more components selected from product components and residual components,
   moving said parts with their components forward in the separation system using a sequence of steps, which steps comprise one or more of a feeding phase, a circulation phase, and an elution phase, and
   withdrawing components of said parts during the same or following separation sequences in one or more residual fractions and/or in one or more recycle fractions and/or in one or more product fractions,
   whereby the volume, introduction position and introduction step of said parts are determined on the basis of the retention volumes of the components of said parts, the volume of the resin bed through which the components of the parts pass and the volume of the steps moving the components of the parts from the introduction position to the calculated target withdrawal position of the components during said same or following separation sequences while essentially maintaining or improving the purity of the product fraction(s) and the yield of the product components.

2. A process as claimed in claim 1, wherein the components of said parts are essentially withdrawn during the following 1 to 4 separation sequences.

3. A process as claimed in claim 1, wherein the chromatographic separation system is a batch system.

4. A process as claimed in claim 1, wherein the chromatographic separation system is a sequential simulated moving bed (SMB) system.

5. A process as claimed in claim 4, wherein the sequential chromatographic SMB system contains one or more loops in the system.

6. A process as claimed in claim 4, wherein the sequential chromatographic SMB system contains one or more separation profiles in a loop.

7. A process as claimed in claim 4, wherein the separation profile is circulated more than once or less than once through the resin bed of the system during one cycle.

8. A process as claimed in claim 1, wherein said sugars are selected from xylose, fructose, glucose, mannose, arabinose, galactose, rhamnose, fucose, sucrose, maltose, levoglucosan, ribose, isomaltulose, tagatose, trehalose, trehalulose, and psicose.

9. A process as claimed in claim 1, wherein said sugars are selected from xylose, fructose, and maltose.

10. A process as claimed in claim 1, wherein said sugar alcohols are selected from xylitol, mannitol, sorbitol, inositol, maltitol, isomalt, and erythritol.

11. A process as claimed in claim 1, wherein said sugar acids are selected from hydroxy acids, carboxylic acids such as aldonic acids, e.g. xylonic acid, gluconic acid, and itaconic acid, and uronic acids, such as glucuronic acid and galacturonic acid.

12. A process as claimed in claim 1, wherein said residual components of said parts are selected from lignosulfonates, oligosaccharides, salts, organic acids, and inorganic acids and salts thereof, color compounds, amino acids, and glycerol as well as sugars, sugar alcohols and sugar acids other than the product sugars, sugar alcohols and sugar acids.

13. A process as claimed in claim 1, wherein said parts have a dry solids content of 0.2 to 50%, preferably 1 to 30%.

14. A process as claimed in claim 1, wherein the xylose content of said parts is in a range of 0 to 75% on DS, preferably 0 to 15% on DS.

15. A process as claimed in claim 1, wherein said one or more parts are front slope parts or rear slope parts of a product component subprofile selected from a sugar subprofile, a sugar alcohol subprofile, a sugar acid subprofile, and a betaine subprofile.

16. A process as claimed in claim 1, wherein said one or more parts are front slope parts and/or rear slope parts of a first product component subprofile,
    they are introduced back to said separation system to replace a portion of the eluent water, and
    during the next sequence said first product component of said front slope and/or rear slope parts is withdrawn in a recycle fraction of a second product component to be recycled to the feed and to be recovered in a first product component fraction.

17. A process as claimed in claim 1, wherein said one or more parts are front slope parts or rear slope parts of a residual subprofile.

18. A process as claimed in claim 17, wherein said front slope parts or rear slope parts of a residual subprofile are introduced back to said separation system to replace a portion of the eluent water, and residual components of said front slope parts or rear slope parts are withdrawn in more than one residual fraction during the same or following 1 to 4 sequences.

19. A process as claimed in claim 1, wherein the volume of said parts is 1 to 50% of the volume of all steps moving the separation profile forward during one separation sequence.

20. A process as claimed in claim 1, wherein the volume of said parts is preferably less than that of the recycle fraction or residue fraction in which the components of said parts are to be withdrawn.

21. A process as claimed in claim 1, wherein said parts are introduced into the separation system as an intact separation profile.

22. A process as claimed in claim 1, wherein said parts are collected into a separate tank and introduced into the separation system from the tank.

23. A process as claimed in claim 1, wherein said parts are selected from
    front slope parts and rear slope parts of a first product component subprofile and front slope parts and rear slope parts of a residual subprofile,
    said parts are introduced back to the separation system to replace a portion of the eluent water,
    the first product component of said parts and/or the residual components of said parts are withdrawn during the next sequence in a recycle fraction of a second product component, which fraction is recycled to the feed, followed by
    recovering the first product component of said parts in the first product component fraction and/or recovering the residual components of said parts in the residual fractions during the following separation sequences.

24. A process as claimed in claim 23, wherein said recycle fractions of the second product component are selected from front slope parts and rear slope parts of a subprofile of the second product component.

25. A process as claimed in claim 1, wherein said solution containing at least one component selected from sugars, sugar alcohols, sugar acids and betaine is a plant-based extract, hydrolysate or a derivative thereof.

26. A process as claimed in claim 1, wherein said solution is selected from a sulfite spent liquor, a starch hydrolysate, and a sugar beet derived solution, such as molasses, stillages, and fermentation products thereof, for example vinasse.

27. A process as claimed in claim 1, wherein said parts are used for substituting 5 to 70% of eluent water.

28. A process as claimed in claim 1, wherein the process provides a product component fraction, where the content of the product component is 35 to 99% on DS.

29. A process as claimed in claim 1, wherein the process provides a xylose product fraction, which has a xylose content of 35 to 80%, preferably 40 to 75%, on DS.

30. A process as claimed in claim 1, wherein the process provides a product component yield in a range of 60 to 98% based on the content of the product component in the feed solution.

31. A process as claimed in claim 1, wherein the process provides a xylose yield of more than 85%, preferably more than 90%, and more preferably more than 95%, based on the content of xylose in the feed solution.

32. A process as claimed in claim 1, wherein said one or more parts of a separation profile are introduced into one or more eluent introduction positions within the same separation system or into one or more eluent introduction positions in other similar parallel separation systems or in different separation systems.

* * * * *